(12) United States Patent
Mori et al.

(10) Patent No.: US 8,509,877 B2
(45) Date of Patent: Aug. 13, 2013

(54) ENDOSCOPE INSERTION SUPPORT SYSTEM AND ENDOSCOPE INSERTION SUPPORT METHOD

(75) Inventors: Kensaku Mori, Nagoya (JP); Takayuki Kitasaka, Nagoya (JP); Shunya Akimoto, Kawasaki (JP); Kouhei Ebe, Hino (JP); Takeshi Wada, Chofu (JP)

(73) Assignee: Olympus Medical Systems Corp., Tokyo (JP)

( * ) Notice: Subject to any disclaimer, the term of this patent is extended or adjusted under 35 U.S.C. 154(b) by 1267 days.

(21) Appl. No.: 12/260,630

(22) Filed: Oct. 29, 2008

(65) Prior Publication Data

US 2009/0054729 A1 Feb. 26, 2009

Related U.S. Application Data

(63) Continuation of application No. PCT/JP2007/059208, filed on Apr. 27, 2007.

(30) Foreign Application Priority Data

May 2, 2006 (JP) ................................ 2006-128682

(51) Int. Cl.
*A61B 5/05* (2006.01)

(52) U.S. Cl.
USPC .......................................... 600/424; 382/128

(58) Field of Classification Search
USPC ........................ 600/424, 262, 434; 382/128
See application file for complete search history.

(56) References Cited

U.S. PATENT DOCUMENTS 6,343,936 B1 * 2/2002 Kaufman et al. ............. 434/262
2004/0220466 A1 11/2004 Matsumoto

FOREIGN PATENT DOCUMENTS

| JP | 2000-135215 | 5/2000 |
| JP | 2004-313736 | 11/2004 |
| JP | 2004-350791 | 12/2004 |

OTHER PUBLICATIONS

Kitasaka, T. et al., "A Method for Extraction of Bronchus Regions from 3D Chest X-ray CT Images by Analyzing Structural Features of the Bronchus", Forma, (2002), pp. 321-338, vol. 17, No. 4.

* cited by examiner

*Primary Examiner* — Unsu Jung
*Assistant Examiner* — Saurel J Selkin
(74) *Attorney, Agent, or Firm* — Scully, Scott, Murphy & Presser, P.C.

(57) ABSTRACT

According to the invention, a VOI (Volume of Interest) generation setting section disposed in an endoscope insertion support apparatus comprises a VOI setting function section, a VOI extending function section, a VOI direction determining function section, a VOI branch determining function section, a VOI resetting function section, a VOI information storage function section, a VOI size determining function section and a VOI branch extracting function section. This configuration enables a VOI to be effectively set in a tubular organ having a strictured part and tubular path area information on the tubular organ to be extracted.

12 Claims, 39 Drawing Sheets

FIG.4

PATIENT INFORMATION

PATIENT ID
00001234

PATIENT NAME
TANAKA TARO

AGE  SEX
45   ● M  ○ F

MODALITY

MODALITY LIST
Modaloty 0 ▼    ADD...    RE-READ IN...

MODALITY NAME
CT

RECEPTION BY DICOM

VOI SETTING

PROCESSING OF BRONCHUS EXTRACTION

INITIAL SHAPE OF NEW VOI=a×a×b0

IF b≤a, VOI EXTENSION=b←b+b0

IF b>a AND Δr>L, NEW VOI PRODUCED

PROCESSING OF BRONCHUS EXTRACTION

ENDOSCOPE INSERTION SUPPORT SYSTEM AND ENDOSCOPE INSERTION SUPPORT METHOD

CROSS REFERENCE TO RELATED APPLICATION

This application is a continuation application of PCT/JP2007/059208 filed on Apr. 27, 2007 and claims benefit of Japanese Application No. 2006-128682 filed in Japan on May 2, 2006, the entire contents of which are incorporated herein by this reference.

BACKGROUND OF THE INVENTION

1. Field of the Invention

The present invention relates to an endoscope insertion support system and an endoscope insertion support method for supporting the insertion of an endoscope into the tubular path of a tubular organ.

2. Description of the Related Art

In recent years, diagnosing by photographic images has come into extensive practice; for instance, three-dimensional image data within a subject are obtained by picking up tomograms of the subject with an X-ray CT (computed tomography) apparatus or the like, and the intended diagnosis is performed by using the three-dimensional image data.

With a CT apparatus, by consecutively shifting the subject in the direction of its bodily axis while consecutively turning X-ray irradiation and detection, a spiral continuous scan (helical scan) is performed on a three-dimensional area of the subject, and a three-dimensional image is produced from consecutively sliced tomograms of the three-dimensional area.

One of such three-dimensional images is a three-dimensional image of the bronchus of a lung. A three-dimensional image of a bronchus is used for three-dimensionally identifying the position of a disordered part suspected of presence of lung cancer or the like. Then, in order to check the disordered part by biopsy, a bronchoscope is inserted and a sample of the tissue is picked up by extruding from its distal end portion a bioptic needle, bioptic forceps or the like.

In a tubular path such as a bronchus having multi-step branches in the body, when the location of the disordered part is near the periphery of a branch, it is difficult to enable the distal end portion of the endoscope to reach the target region in a short period of time.

For this reason, for instance Japanese Patent Application Laid-Open No. 2000-135215 as Document 1 proposes an apparatus by which (1) a three-dimensional image of a tubular path in a subject is produced on the basis of image data of a three-dimensional area in the subject, (2) the route to the target point is figured out along the tubular path on the three-dimensional image, (3) a virtual endoscopic image of the tubular path along the route is produced on the basis of the image data, and (4) a bronchoscope is navigated to the target region by displaying the virtual endoscopic image.

Also, in order to produce a three-dimensional image of a tubular path in a subject on the basis of image data of a three-dimensional area in the subject, it is necessary to extract area information of the targeted organ, for instance the bronchus (information of how the bronchial branches and connected to constitute the whole bronchus), from the image data of the three-dimensional area.

Then, in "T. Kitasaka, K. Mori, J. Hasegawa and J. Toriwaki; A Method for Extraction of Bronchus Regions from 3D Chest X-ray CT Image by Analyzing Structural Features of the Bronchus", Form a 17, pp. 321-338 (2002) as Document 2 for instance and elsewhere, there is proposed a method, so-called segmentation processing, whereby a VOI (Volume of Interest) of a prescribed size comprising prescribed voxels is set on a three-dimensional area in a subject and area information on a target organ, for instance the bronchus is extracted from image data of the three-dimensional area in the subject within the VOI while installing the VOI in the running direction of the tubular organ.

SUMMARY OF THE INVENTION

An endoscope insertion support system of one aspect of the present invention is provided with: a volume area setting section for setting a volume area which has a start point set in a tubular path of a tubular organ within three-dimensional image data of a subject and has a size so prescribed as to contain the tubular organ; an organ area information calculating section which extracts tubular area information in the volume area on the basis of the three-dimensional image data of the tubular organ in the volume area and calculates segmentation data representing a tubular path shape; a contained state determining section which determines whether or not the tubular path is contained in the volume area set by the volume area setting section; a heteromorphic state detecting section which detects a heteromorphic state of the tubular path shape on the basis of a result of calculation of the organ area information; and a hierarchical volume area setting section which sets a hierarchical volume area obtained by hierarchically linking to the volume area set by the volume area setting section to a size based on a result of determination by the contained state determining section and a result of detection by the heteromorphic state detecting section.

Such the endoscope insertion support system has an effect of enabling a volume area to be effectively set in a tubular organ having a heteromorphic part and tubular path area information on the tubular organ to be correctly extracted.

Furthermore, in the endo scope insertion support system, it is preferable that the hierarchical volume area setting section sets a next-step hierarchical volume area which further hierarchically links to the hierarchical volume area, the organ area information calculating section calculates segmentation data representing a tubular path shape in the next-step hierarchical volume area, the heteromorphic state detecting section detects a heteromorphic state of the tubular path shape in the hierarchical volume area on the basis of a result of calculation of the organ area information, and the hierarchical volume area setting section controls the size of the next-step hierarchical volume area on the basis of the detected heteromorphic state.

Such the endoscope insertion support system has an effect of enabling a volume area to be effectively set in a tubular organ having a region bent at or beyond a prescribed curvature and area information on the tubular organ to be correctly extracted.

Furthermore, the endoscope insertion support system preferably further includes a volume area altering section which extends or contracts a distance between end faces of the volume area.

Such the endoscope insertion support system has an effect of enabling a volume area to be effectively set in a noted part in a tubular organ and area information on the tubular organ to be correctly extracted.

Furthermore, the endoscope insertion support system preferably further includes a direction determining section which determines the extending/contracting direction of the volume area or the hierarchical volume area, and the volume area altering section extends or contracts the distance between the end faces of the volume area or the hierarchical volume area on the basis of a result of determination by the direction determining section.

Such the endoscope insertion support system has an effect of enabling the extending/contracting direction of the volume area or the hierarchical volume area appropriately to match the shape of the tubular path and processing time to be shortened.

Furthermore, in the endoscope insertion support system, it is preferable that the heteromorphic state detecting section detects as at least a heteromorphic state a strictured or expanded state of the tubular path in an end section of the hierarchical volume area on the basis of at least one of a diameter, area and circumferential length out of the segmentation data.

Since such the endoscope insertion support system detects as a heteromorphic state a strictured or expanded state of the tubular path in the end section of the hierarchical volume area in relation to at least one of a diameter, area and circumferential length out of the segmentation data, the endoscope insertion support system is capable of detecting a heteromorphic state similarly to an actual system.

Furthermore, in the endoscope insertion support system, it is preferable that the contained state determining section determines the contained state of the tubular path on the basis of detection of branching hole in the tubular path in an end face of the volume area or the hierarchical volume area.

Such the endoscope insertion support system has an effect of enabling the contained state of the tubular path in the volume area or the hierarchical volume area to be appropriately determined and area information on the tubular organ to be correctly extracted.

Furthermore, in the endoscope insertion support system, it is preferable that the contained state determining section determines the contained state of the tubular path organ on the basis of detection of the tubular organ on a side face of the volume area or the hierarchical volume area.

Such the endoscope insertion support system has an effect of enabling the contained state of the tubular path in the volume area or the hierarchical volume area to be appropriately determined and area information on the tubular organ to be correctly extracted.

Furthermore, the endoscope insertion support system preferably further includes a route setting section which sets a line connecting gravity center points of tubular path sections at least in the vicinities of end faces of the volume area and the hierarchical volume area as a substantial center line to be an endoscope insertion support route.

Such the endoscope insertion support system has an effect of achieving nothing inferior to a locus of the endoscope tip at the time of inserting an actual endoscope by having the route pass the gravity center points of tubular path sections.

Furthermore, in the endo scope insertion support system, it is preferable that the endoscopic insertion support route is set by curvilinearly correcting the substantial center line.

Such the endoscope insertion support system has an effect of achieving nothing inferior to the locus of the endoscope tip at the time of inserting an actual endoscope by making route a smooth curve.

Furthermore, the endoscope insertion support system preferably further includes: a multiplanar reformation image generating section which generates a multiplanar reformation image in the subject on the basis of the three-dimensional image data of the subject; and a start point designating section which designates the start point on the generated multiplanar reformation image.

Such the endoscope insertion support system has an effect of enabling a position intended by a user to be accurately acquired by having the start point designated on the multiplanar reformation image.

Furthermore, in the endoscope insertion support system, it is preferable that coordinates of the start point designated by the start point coordinates designating section are coordinates near the end faces of the volume area or the hierarchical volume area.

Such the endoscope insertion support system has an effect of enabling organ to be extracted from the vicinity of the start point, any unintended area of the organ to be prevented from extraction and the processing time to be shortened.

Furthermore, in the endoscope insertion support system, it is preferable that the tubular organ is one of bronchus, blood vessel, large intestine, small intestine or lymphatic vessel.

Such the endoscope insertion support system has an effect of enabling appropriate endoscopic diagnosis and treatment to be accomplished by presenting tubular information on any one of bronchus, blood vessel, large intestine, small intestine, pancreas duct, bile duct or lymphatic vessel.

The present invention has an effect of enabling a VOI (Volume of Interest) to be effectively set in a tubular organ having a strictured part and tubular path area information on a tubular organ to be correctly extracted.

BRIEF DESCRIPTION OF THE DRAWINGS

FIG. 4 is a diagram showing a patient information selecting screen developed by the processing of FIG. 3;

DETAILED DESCRIPTION OF THE PREFERRED EMBODIMENTS

Figure 1:
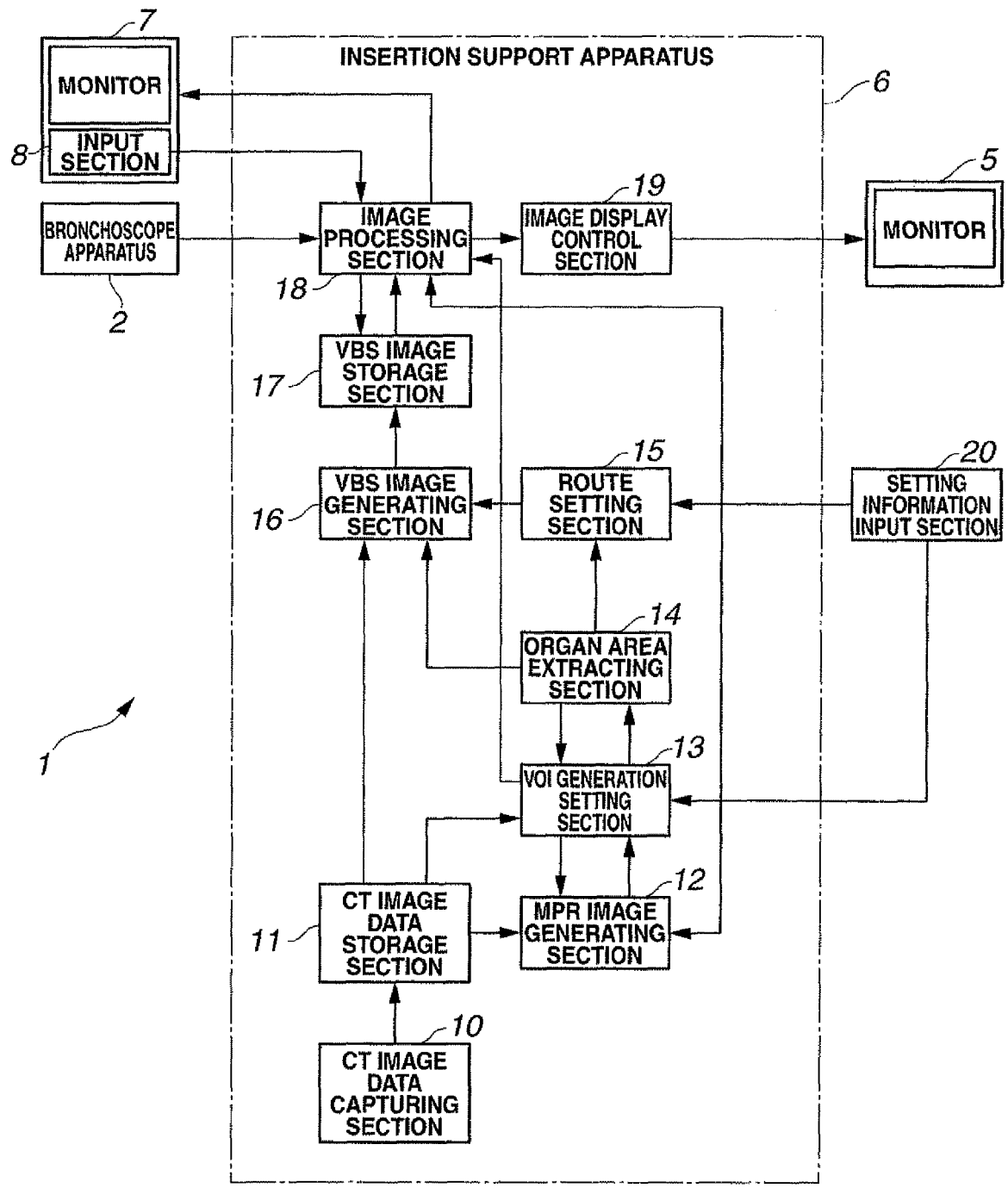
FIG. 1 is a configurational diagram showing the configuration of a bronchoscope insertion support system pertaining to Embodiment 1 of the invention.

Embodiments of the present invention will be described below while referring to the drawings.

Embodiment 1

Figure 2:
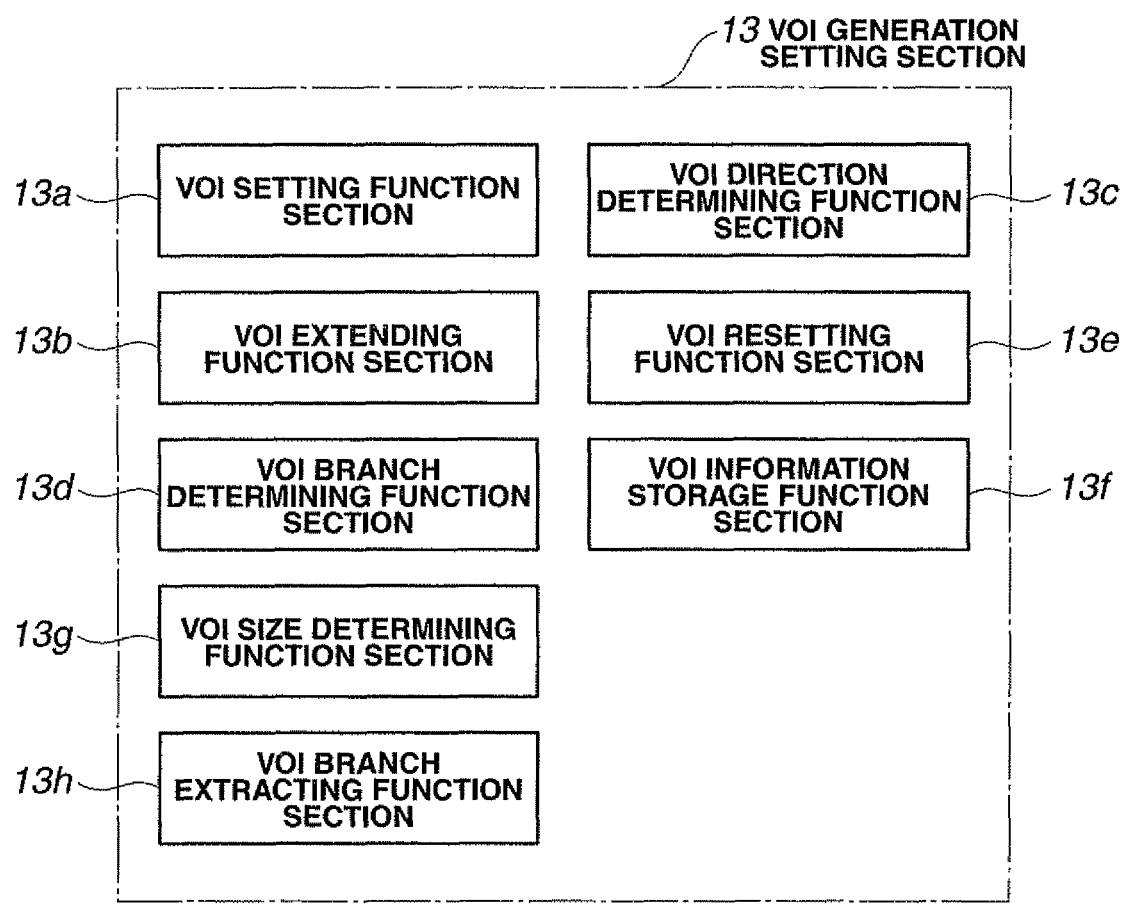
FIG. 2 is a functional block diagram showing the configuration of the VOI generation setting section of FIG. 1.
Figure 3:
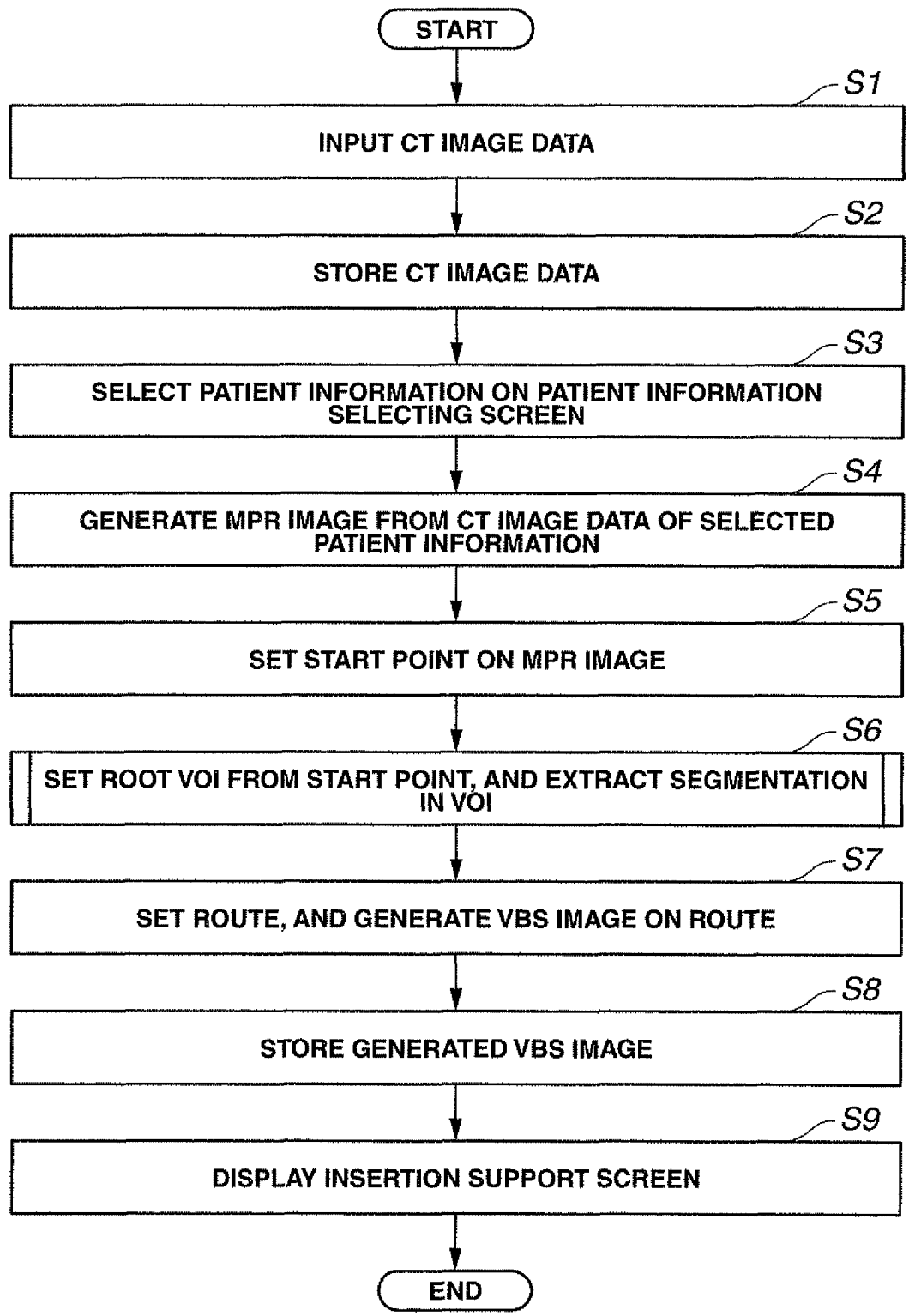
FIG. 3 is a flow chart illustrating the actions of the bronchoscope insertion support system of FIG. 1.
Figure 5:
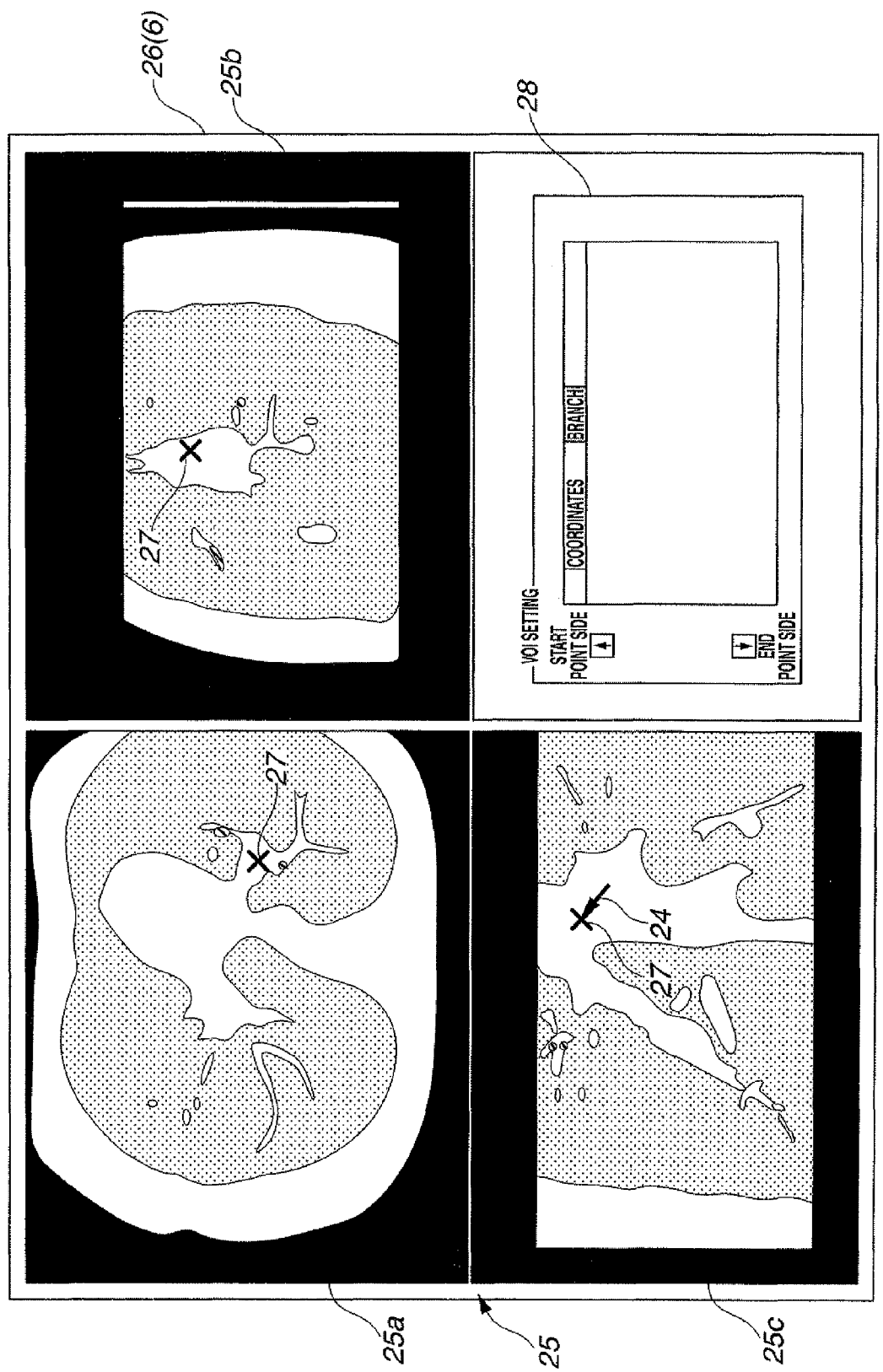
FIG. 5 is a diagram showing an MPR screen generated by the MPR image generating section of FIG. 1.
Figure 6:
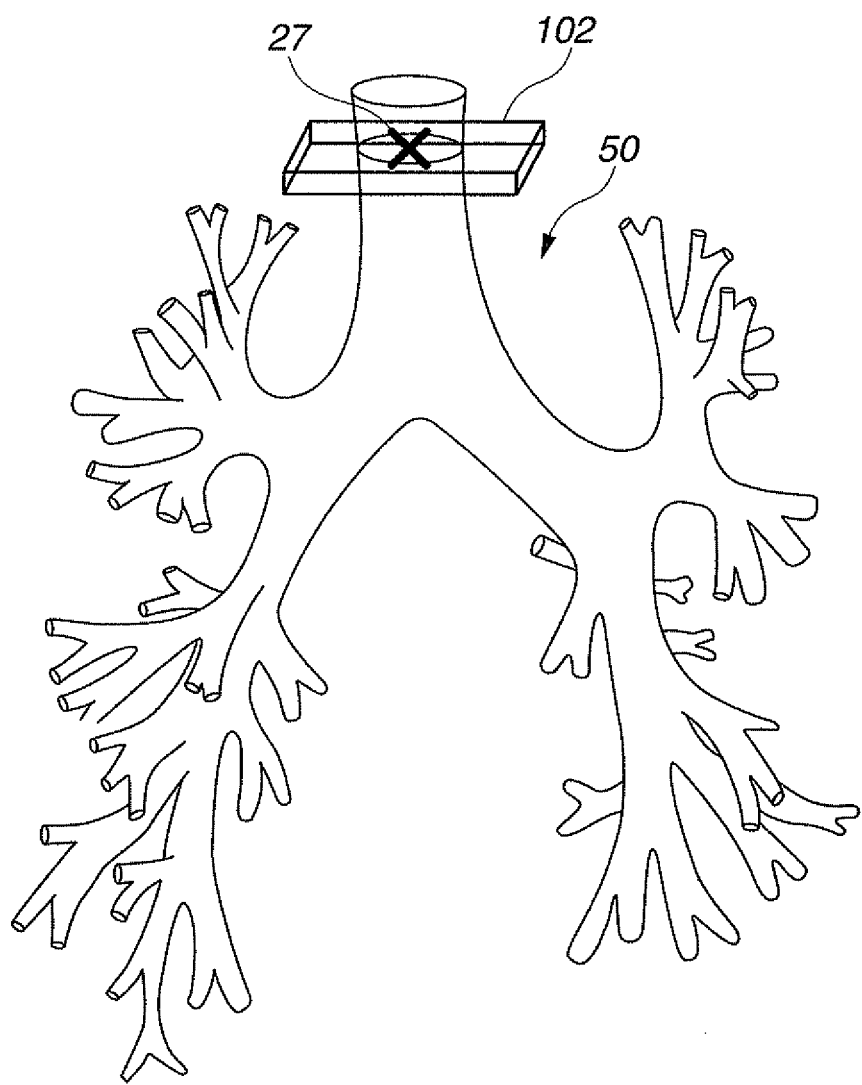
FIG. 6 is a schematic diagram of a bronchus schematically showing a start point set on the MPR screen of FIG. 5.
Figure 7:
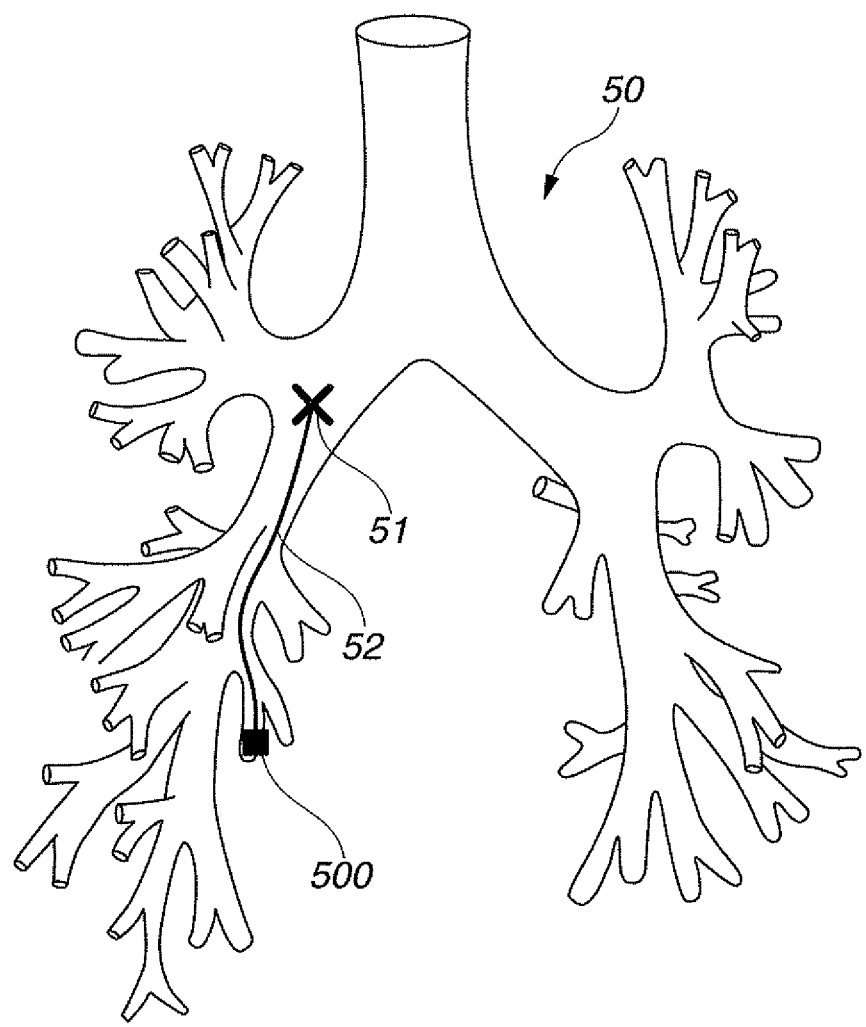
FIG. 7 is a schematic diagram of a bronchus schematically showing a route set on the MPR screen of FIG. 5.
Figure 8:
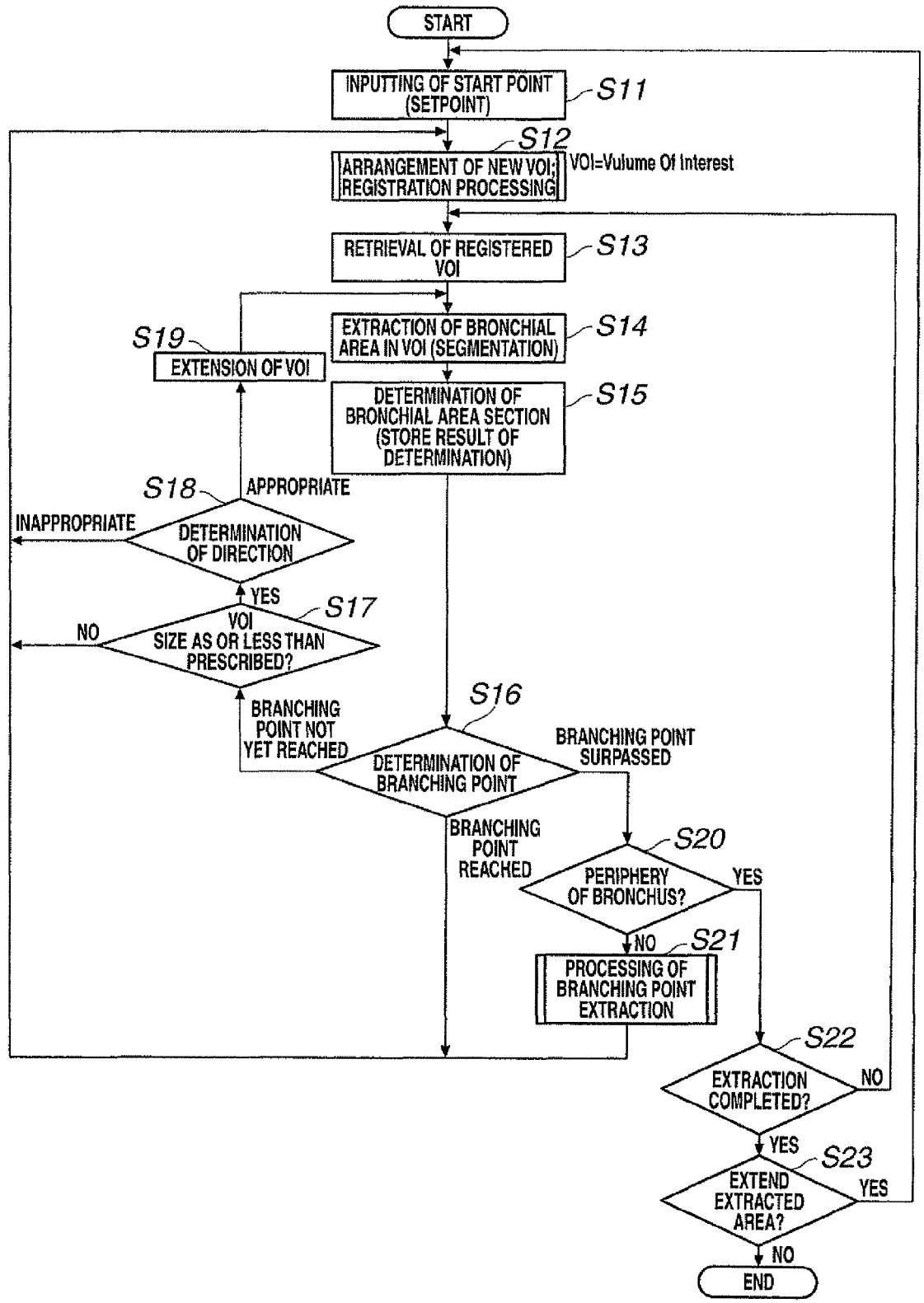
FIG. 8 is a flow chart showing the flow of processing of FIG. 3 to extract bronchial area information.
Figure 9:
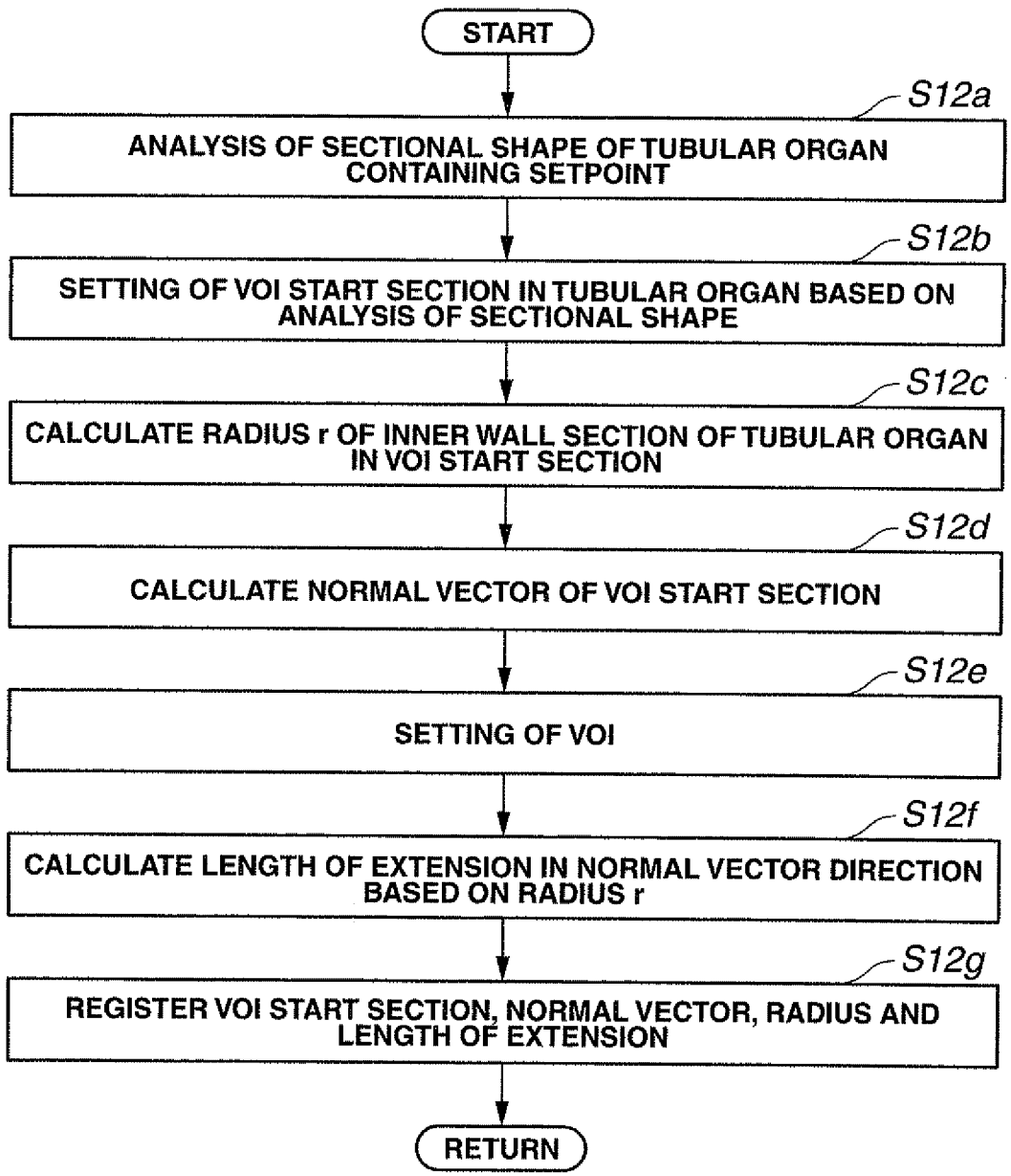
FIG. 9 is a flow chart showing the flow of processing of FIG. 8 to arrange and register a new VOI.
Figure 54:
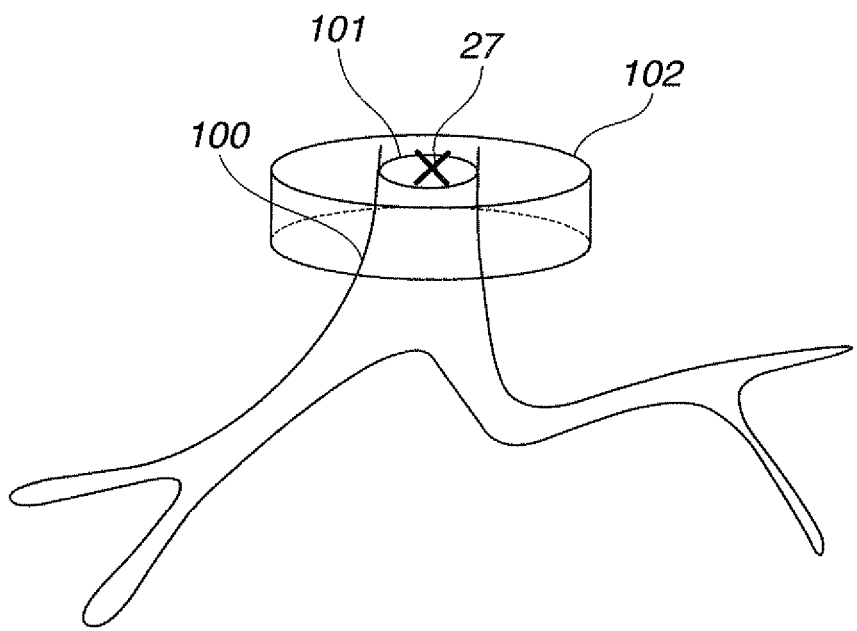
FIG. 54 is a drawing showing a modified example of a VOI generated by the VOI generation setting section of FIG. 1.

FIG. 1 through FIG. 54 pertain to Embodiment 1 of the invention, wherein FIG. 1 is a configurational diagram showing the configuration of a bronchoscope insertion support system; FIG. 2, a functional block diagram showing the configuration of the VOI generation setting section of FIG. 1; FIG. 3, a flow chart illustrating the actions of the bronchoscope insertion support system of FIG. 1; FIG. 4, a diagram showing a patient information selecting screen developed by the processing of FIG. 3; FIG. 5, a diagram showing an MPR screen generated by the MPR image generating section of FIG. 1; FIG. 6, a schematic diagram of a bronchus schematically showing a start point set on the MPR (multiplanar reformation image) screen of FIG. 5; FIG. 7, a schematic diagram of a bronchus schematically showing a route set on the MPR screen of FIG. 5; FIG. 8, a flow chart showing the flow of processing of FIG. 3 to extract bronchial area information; FIG. 9 is a flow chart showing the flow of processing of FIG. 8 to arrange and register a new VOI; and FIG. 10, a first drawing illustrating the processing of FIG. 8 to extract bronchial area information.

Figure 11:
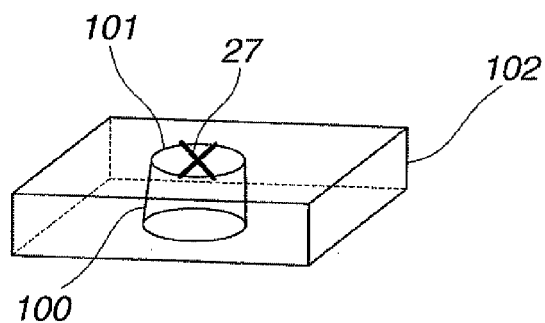
FIG. 11 is a second drawing illustrating the processing of FIG. 8 to extract bronchial area information.
Figure 12:
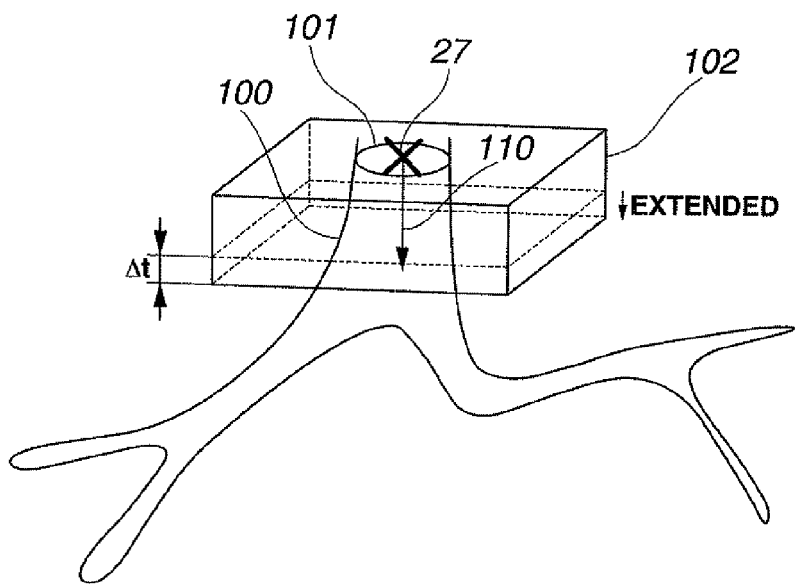
FIG. 12 is a third drawing illustrating the processing of FIG. 8 to extract bronchial area information.
Figure 13:
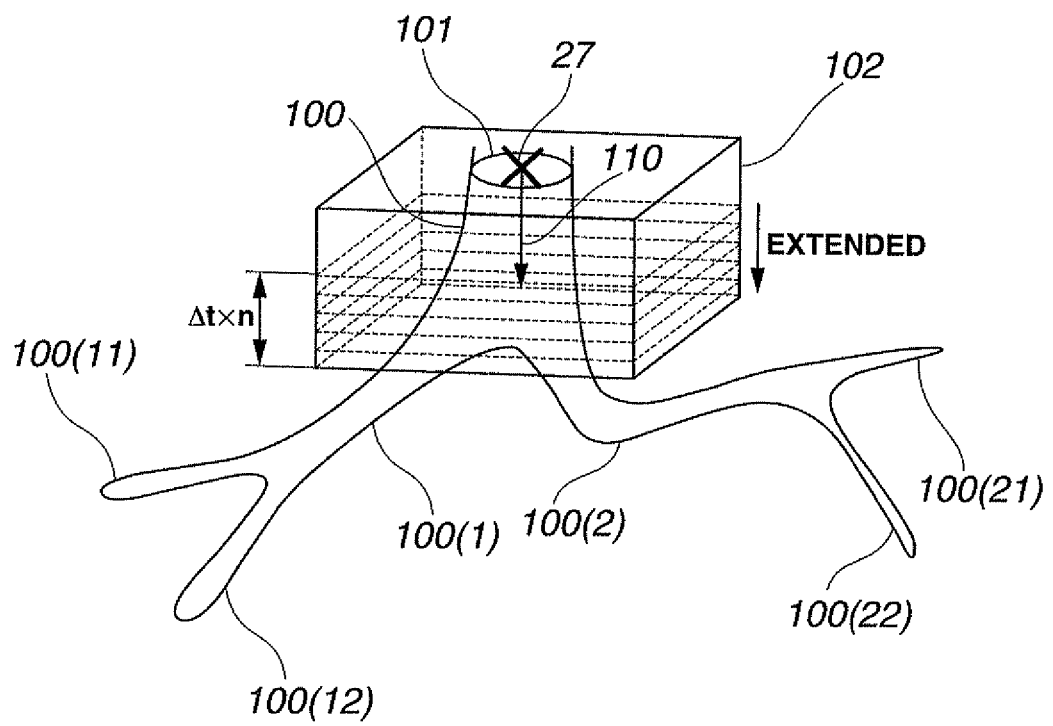
FIG. 13 is a fourth drawing illustrating the processing of FIG. 8 to extract bronchial area information.
Figure 14:
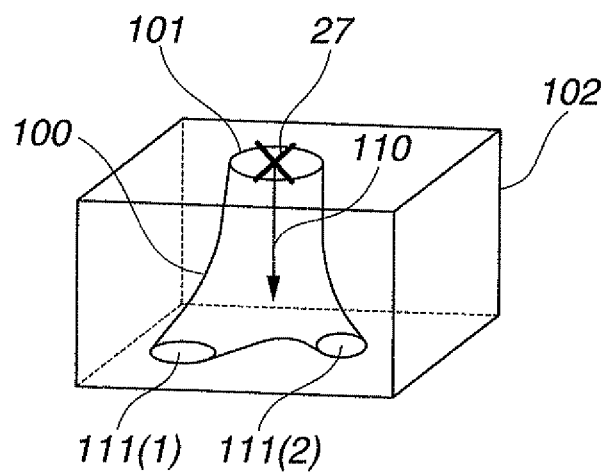
FIG. 14 is a fifth drawing illustrating the processing of FIG. 8 to extract bronchial area information.
Figure 15:
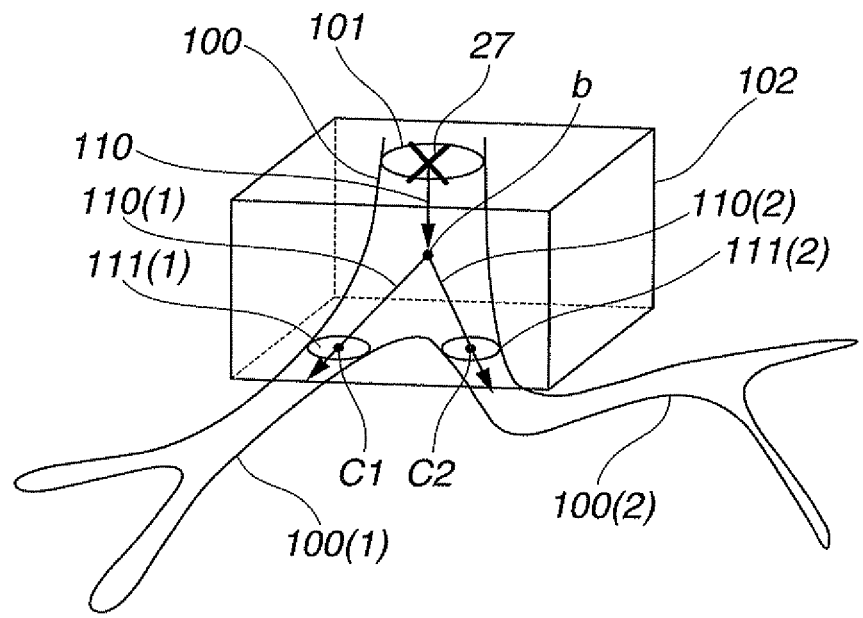
FIG. 15 is a sixth drawing illustrating the processing of FIG. 8 to extract bronchial area information.
Figure 16:
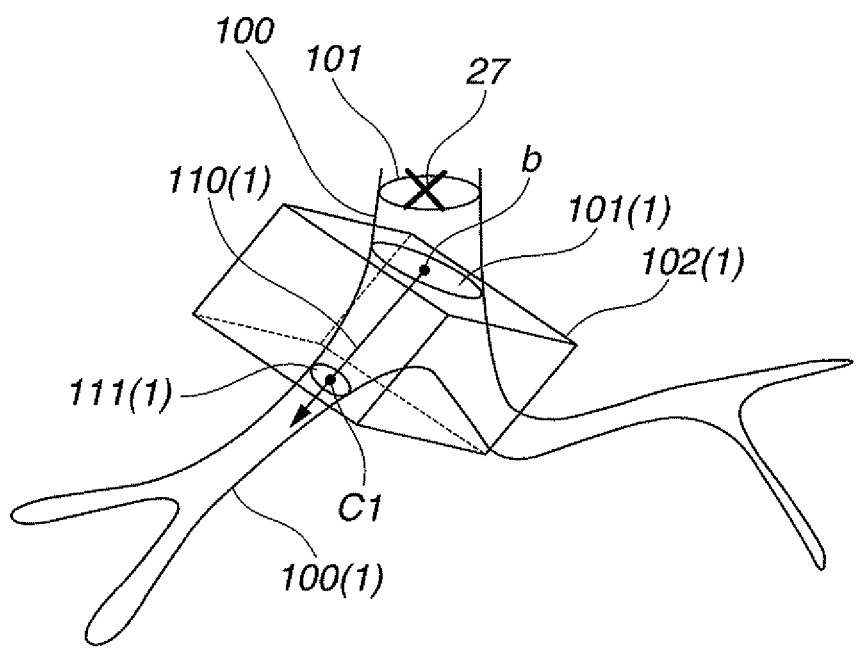
FIG. 16 is a seventh drawing illustrating the processing of FIG. 8 to extract bronchial area information.
Figure 17:
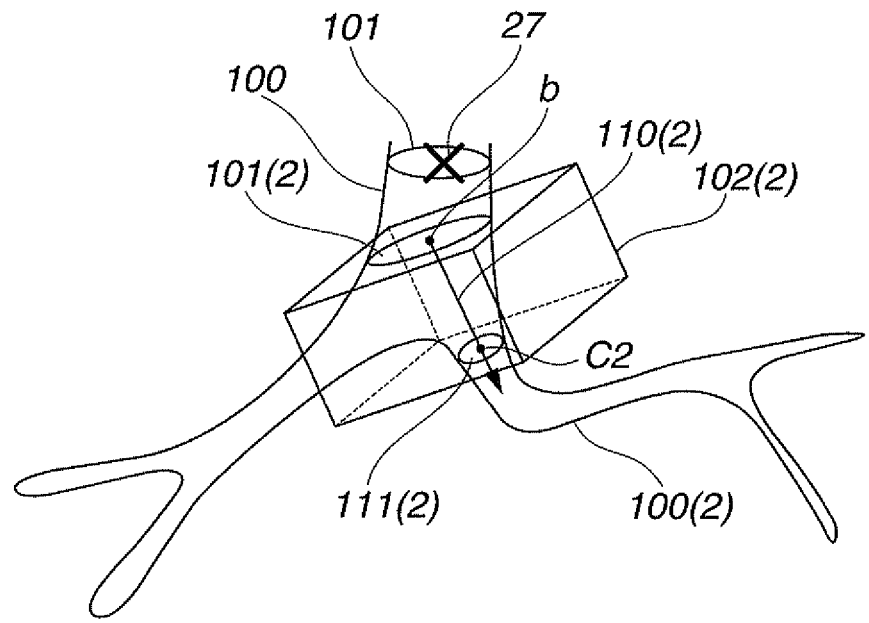
FIG. 17 is an eighth drawing illustrating the processing of FIG. 8 to extract bronchial area information.
Figure 18:
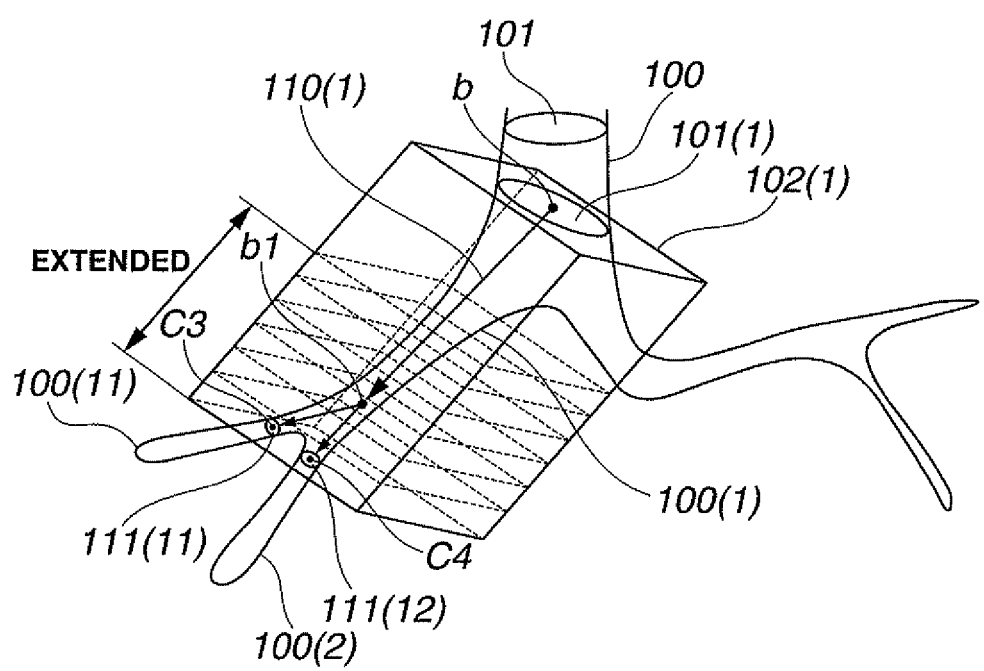
FIG. 18 is a ninth drawing illustrating the processing of FIG. 8 to extract bronchial area information.
Figure 19:
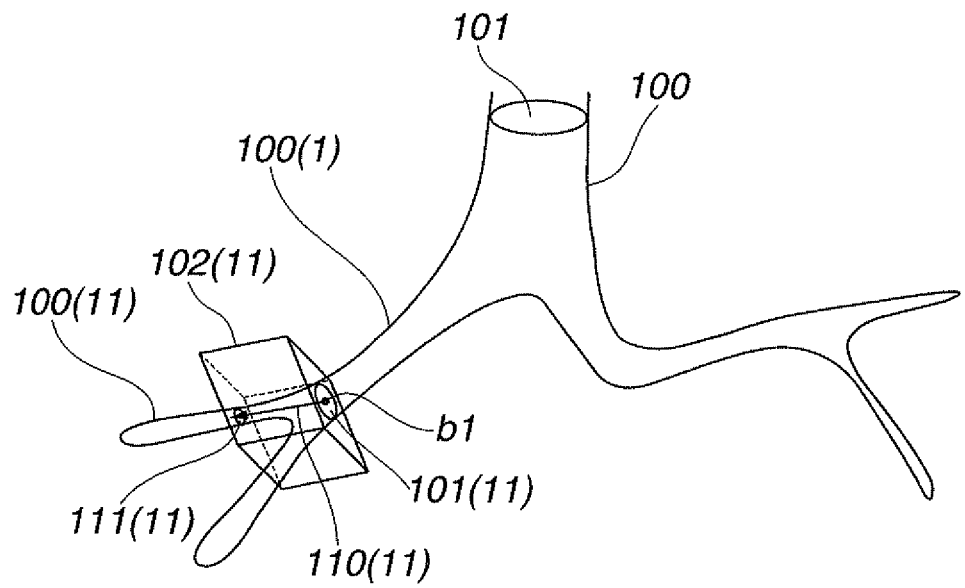
FIG. 19 is a 10th drawing illustrating the processing of FIG. 8 to extract bronchial area information.

FIG. 11 is a second drawing illustrating the processing of FIG. 8 to extract bronchial area information; FIG. 12, a third drawing illustrating the processing of FIG. 8 to extract bronchial area information; FIG. 13, a fourth drawing illustrating the processing of FIG. 8 to extract bronchial area information; FIG. 14, a fifth drawing illustrating the processing of FIG. 8 to extract bronchial area information; FIG. 15, a sixth drawing illustrating the processing of FIG. 8 to extract bronchial area information; FIG. 16, a seventh drawing illustrating the processing of FIG. 8 to extract bronchial area information; FIG. 17, an eighth drawing illustrating the processing of FIG. 8 to extract bronchial area information; FIG. 18, a ninth drawing illustrating the processing of FIG. 8 to extract bronchial area information; FIG. 19, a 10th drawing illustrating the processing of FIG. 8 to extract bronchial area information; and FIG. 20, an 11th drawing illustrating the processing of FIG. 8 to extract bronchial area information.

Figure 21:
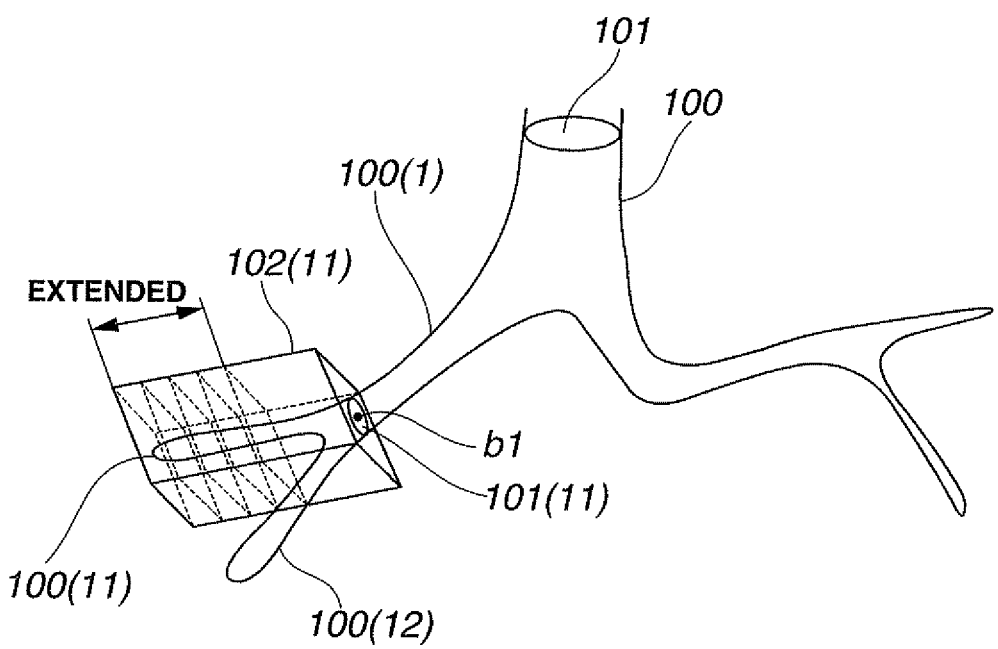
FIG. 21 is a 12th drawing illustrating the processing of FIG. 8 to extract bronchial area information.
Figure 22:
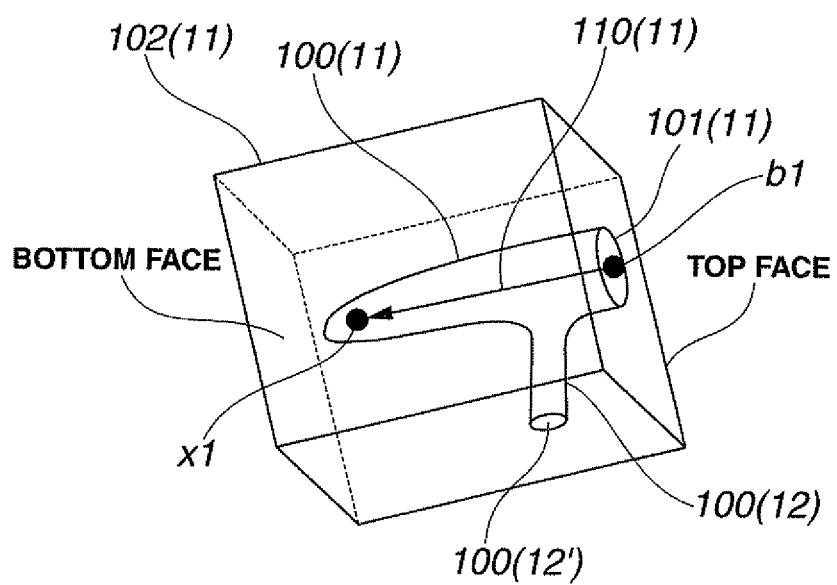
FIG. 22 is a 13th drawing illustrating the processing of FIG. 8 to extract bronchial area information.
Figure 23:
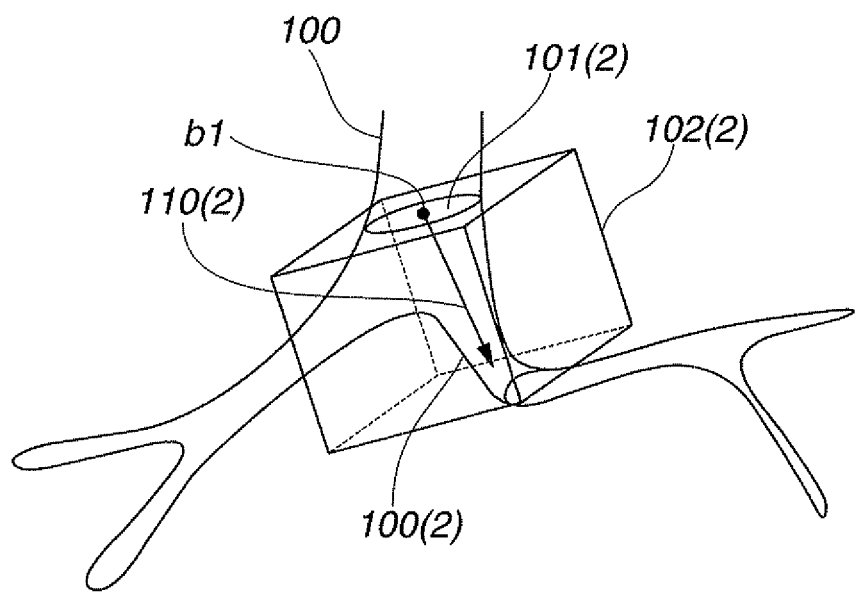
FIG. 23 is a 14th drawing illustrating the processing of FIG. 8 to extract bronchial area information.
Figure 24:
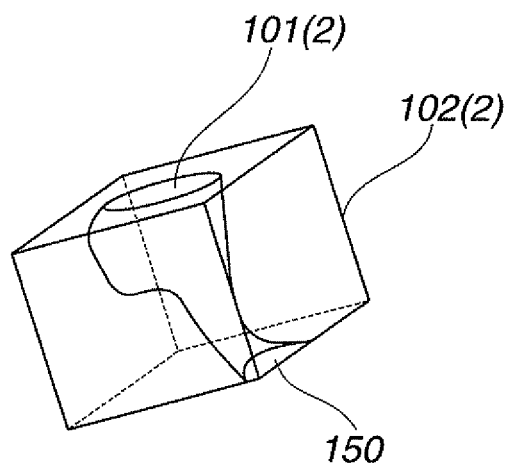
FIG. 24 is a 15th drawing illustrating the processing of FIG. 8 to extract bronchial area information.
Figure 25:
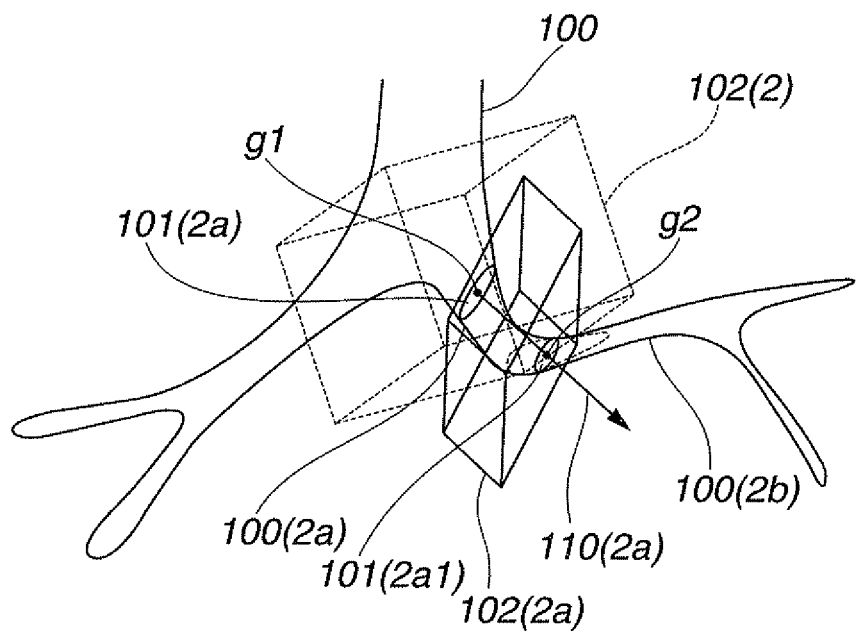
FIG. 25 is a 16th drawing illustrating the processing of FIG. 8 to extract bronchial area information.
Figure 26:
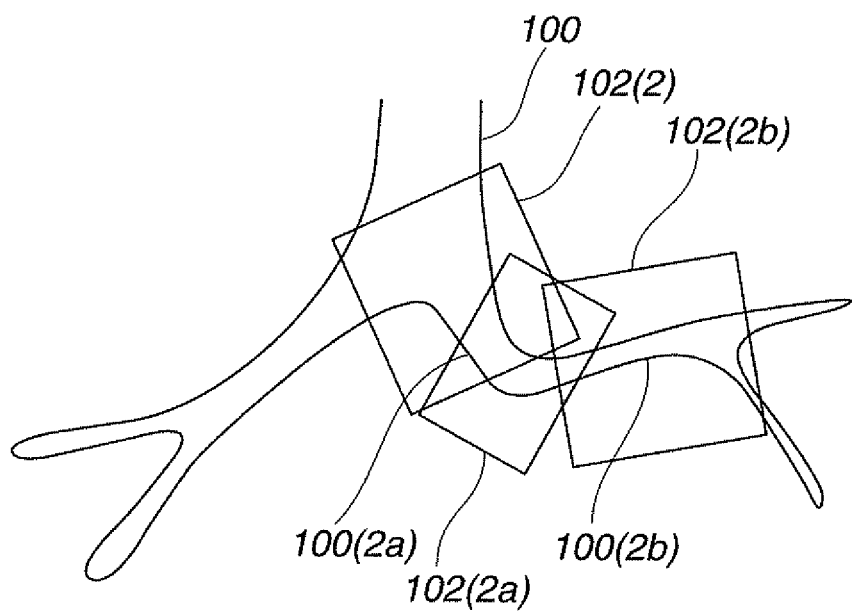
FIG. 26 is a 17th drawing illustrating the processing of FIG. 8 to extract bronchial area information.
Figure 27:
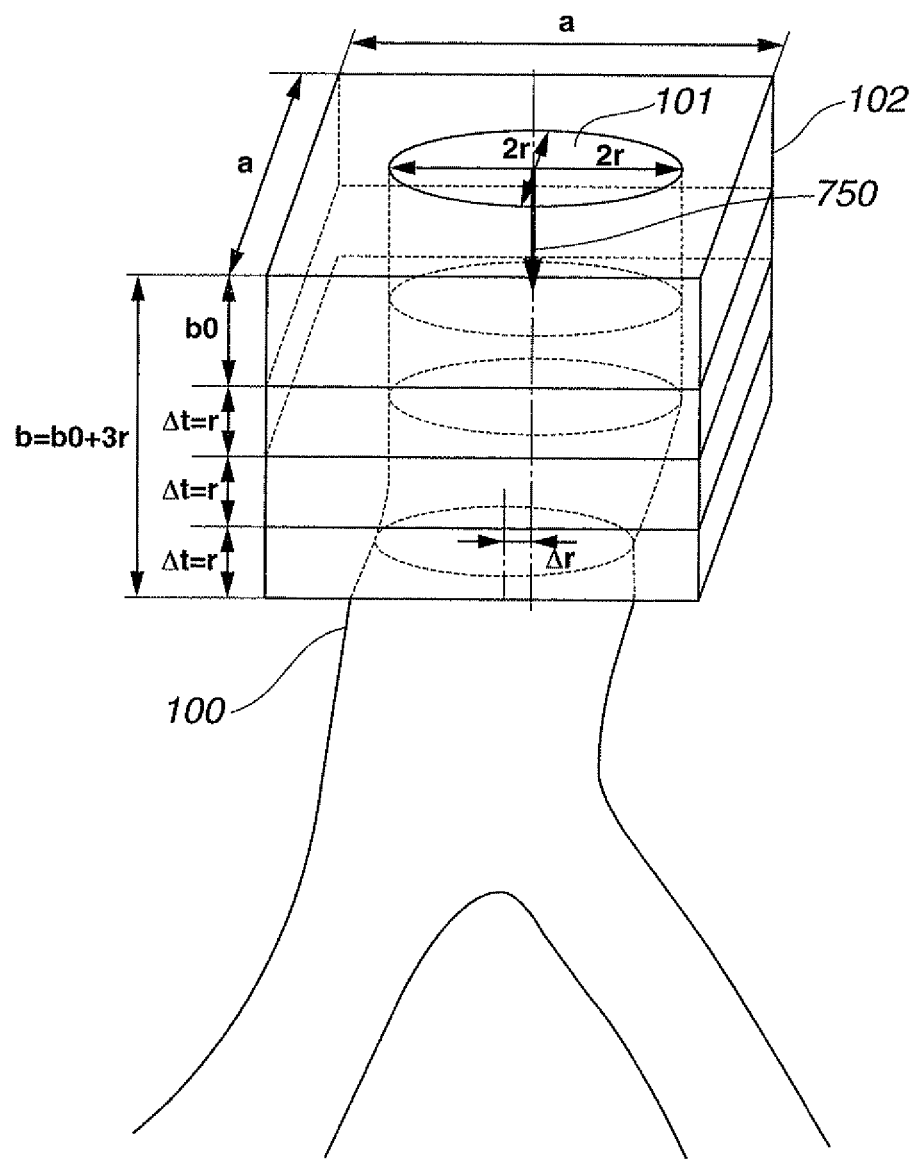
FIG. 27 is a first drawing illustrating the processing to arrange and register a new VOI of FIG. 9.
Figure 28:
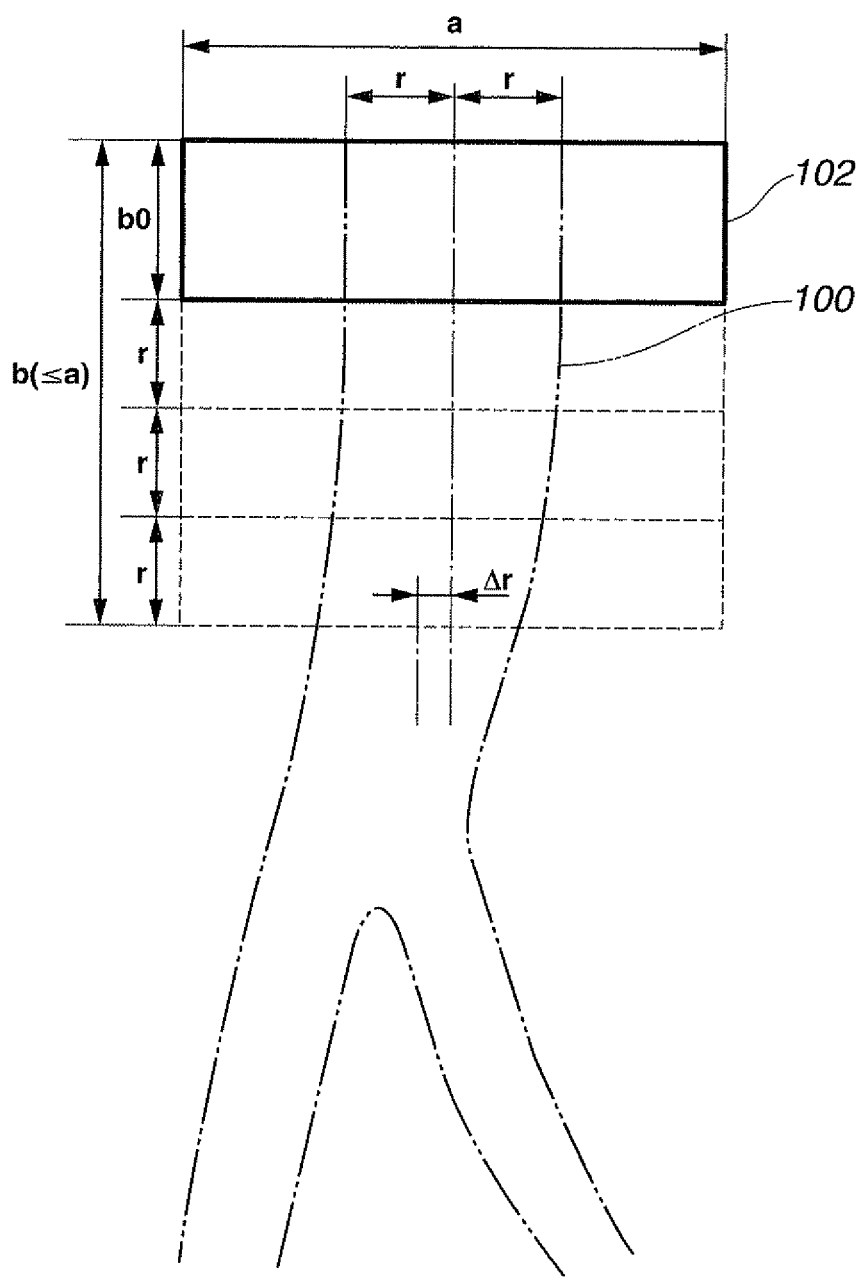
FIG. 28 is a second drawing illustrating the processing to arrange and register a new VOI of FIG. 9.
Figure 29:
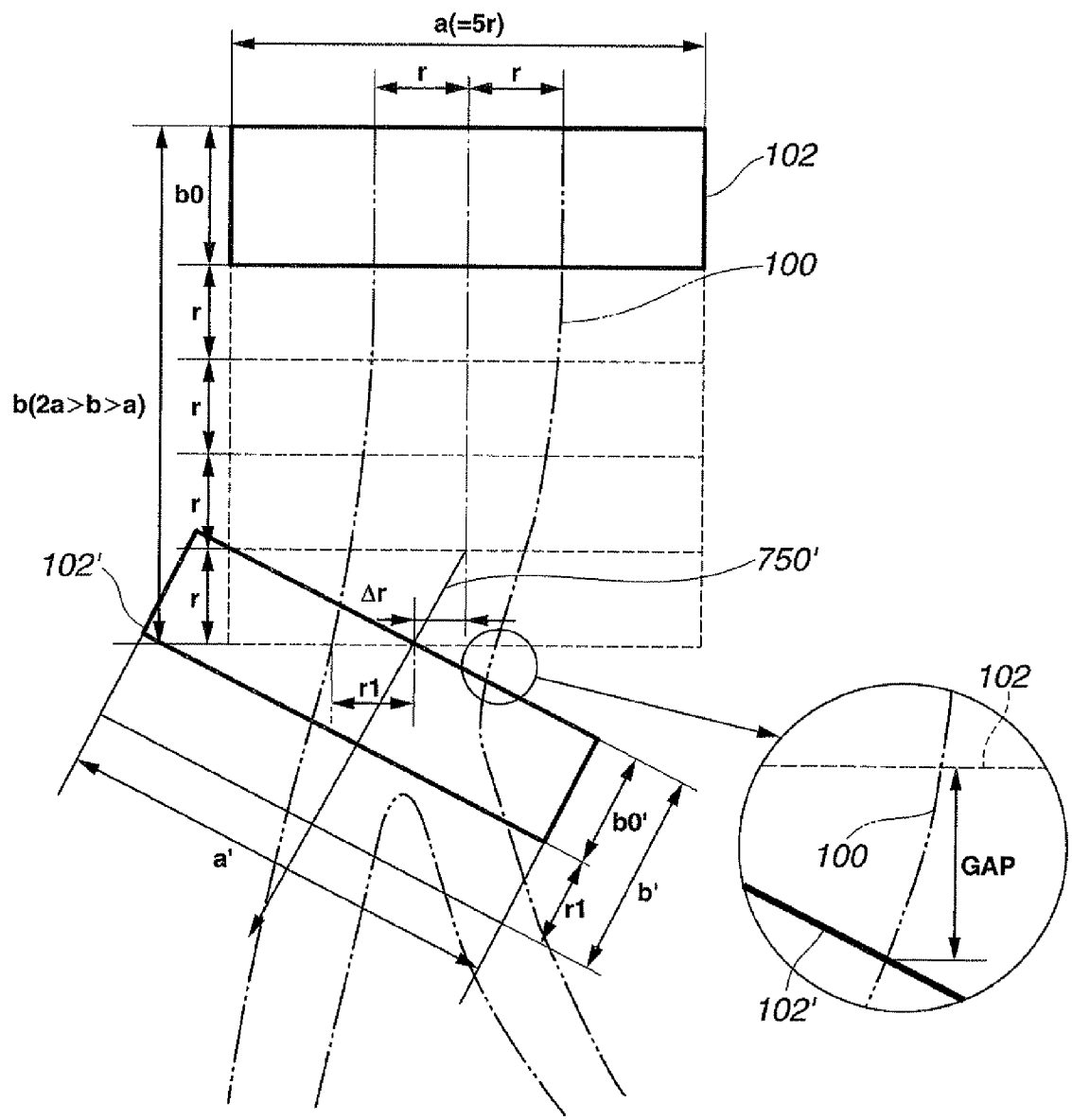
FIG. 29 is a third drawing illustrating the processing to arrange and register a new VOI of FIG. 9.

FIG. 21 is a 12th drawing illustrating the processing of FIG. 8 to extract bronchial area information; FIG. 22, a 13th drawing illustrating the processing of FIG. 8 to extract bronchial area information; FIG. 23, a 14th drawing illustrating the processing of FIG. 8 to extract bronchial area information; FIG. 24, a 15th drawing illustrating the processing of FIG. 8 to extract bronchial area information; FIG. 25, a 16th drawing illustrating the processing of FIG. 8 to extract bronchial area information; FIG. 26, a 17th drawing illustrating the processing of FIG. 8 to extract bronchial area information; FIG. 27, a first drawing illustrating the processing to arrange and register a new VOI of FIG. 9; FIG. 28, a second drawing illustrating the processing to arrange and register a new VOI of FIG. 9; FIG. 29 is a third drawing illustrating the processing to arrange and register a new VOI of FIG. 9; and FIG. 30, a fourth drawing illustrating the processing to arrange and register a new VOI of FIG. 9.

Figure 31:
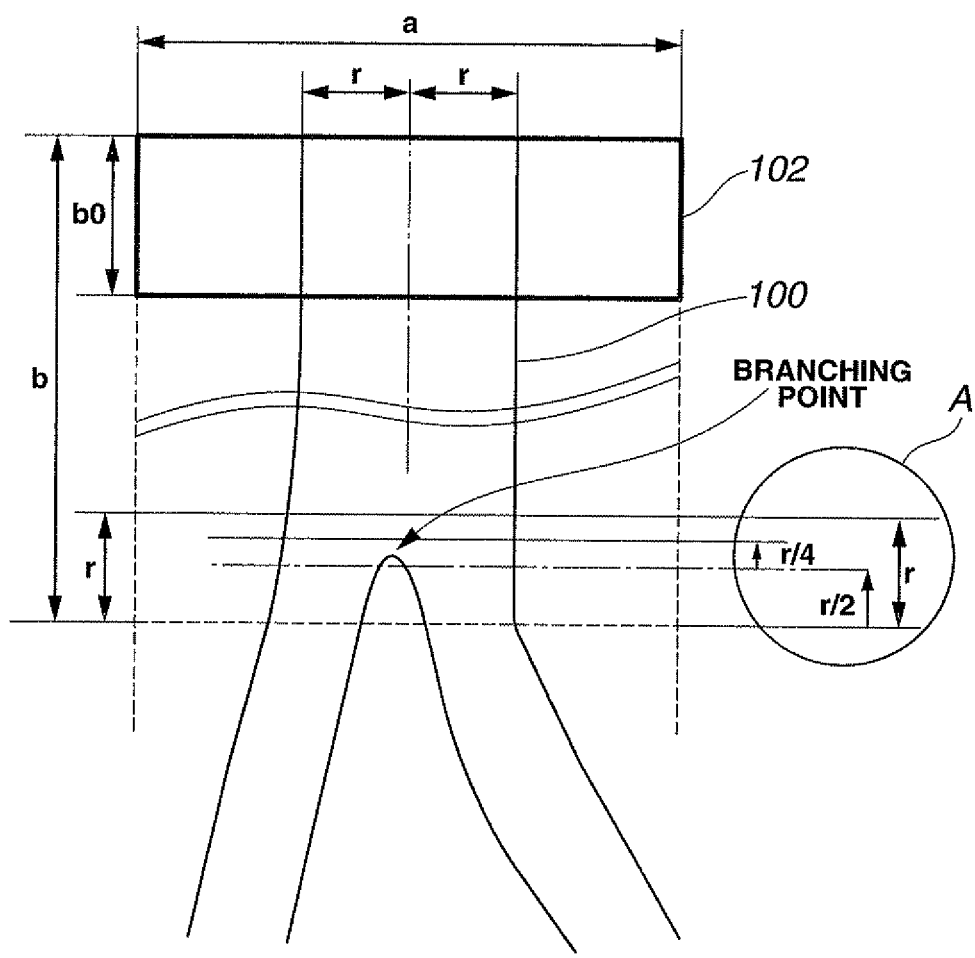
FIG. 31 is a first drawing illustrating the processing of FIG. 8 to extract a branching point.
Figure 32:
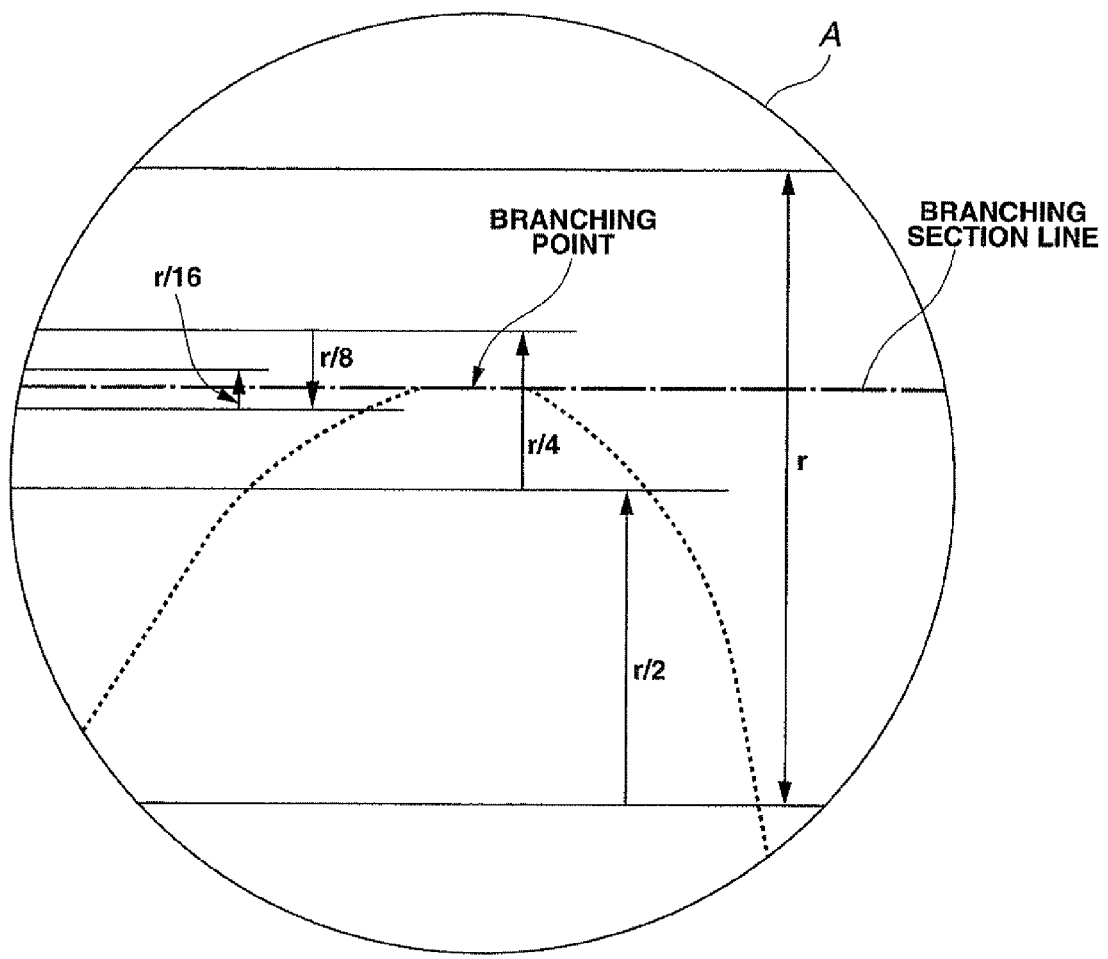
FIG. 32 is a second drawing illustrating the processing of FIG. 8 to extract a branching point.
Figure 33:
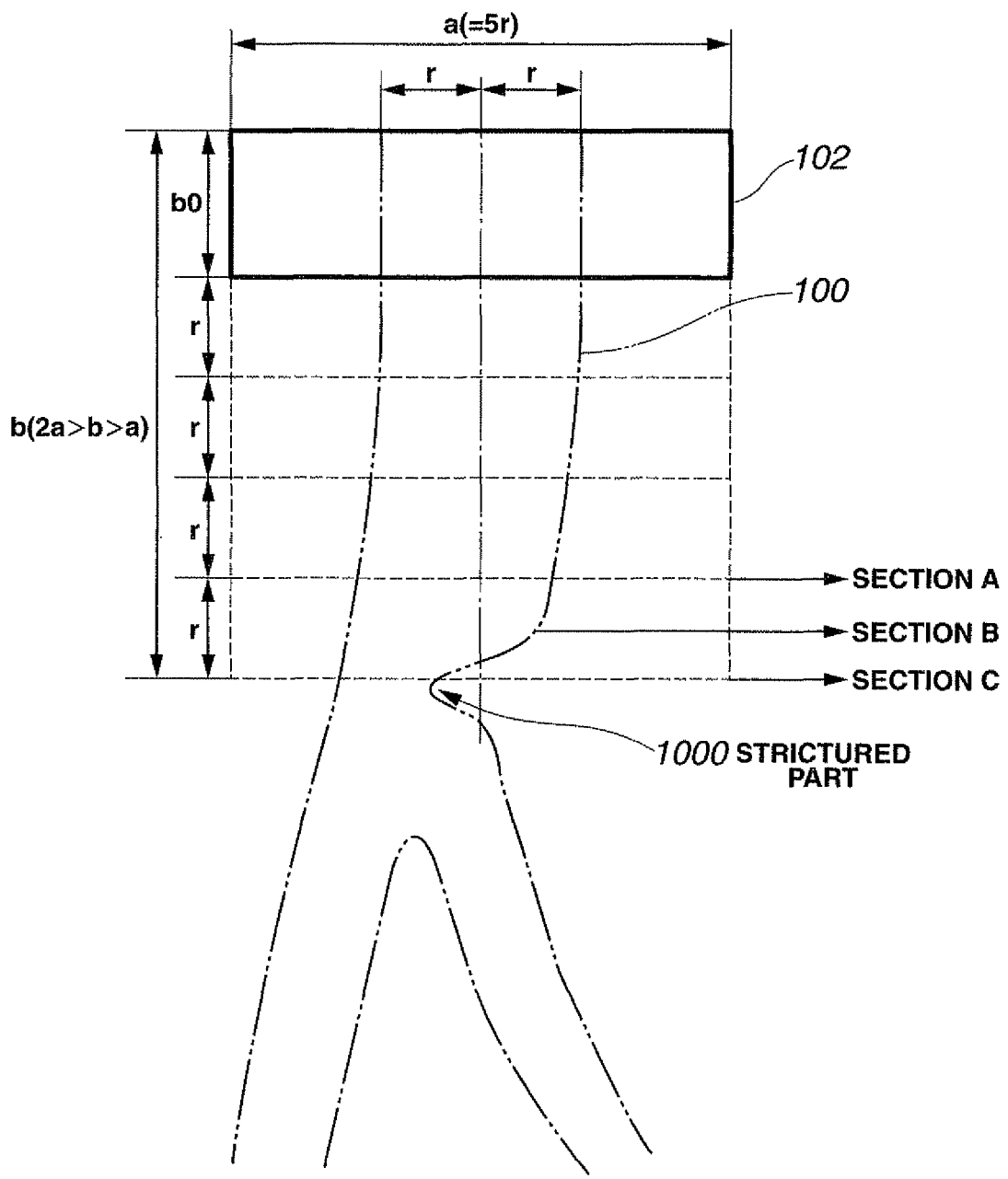
FIG. 33 is a first drawing illustrating the processing of FIG. 8 to determine a bronchial area section.
Figure 34:
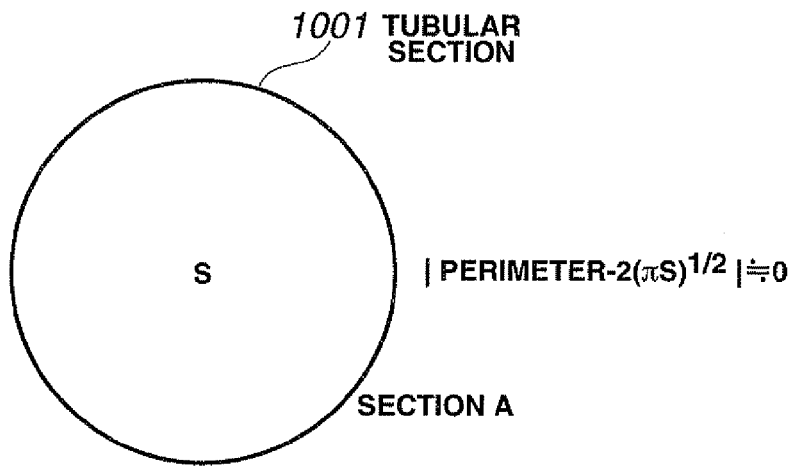
FIG. 34 is a second drawing illustrating the processing of FIG. 8 to determine a bronchial area section.
Figure 35:
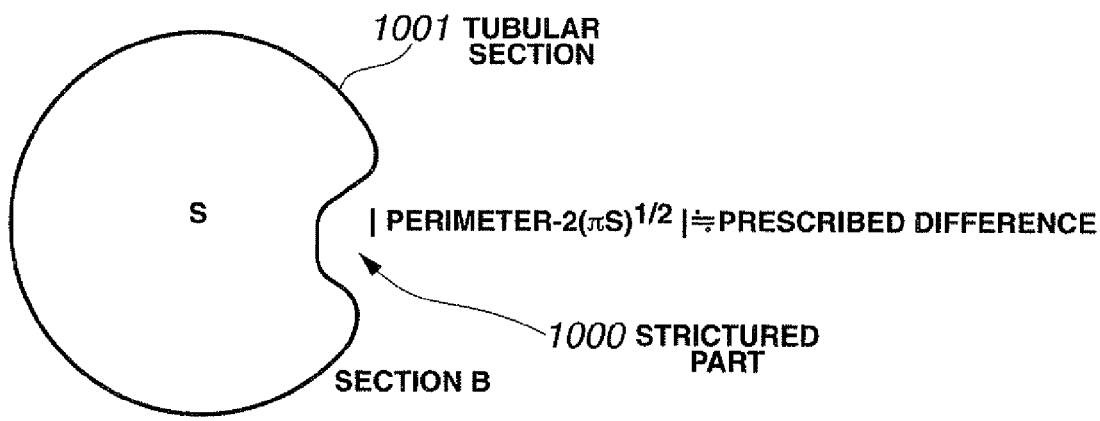
FIG. 35 is a third drawing illustrating the processing of FIG. 8 to determine a bronchial area section.
Figure 36:
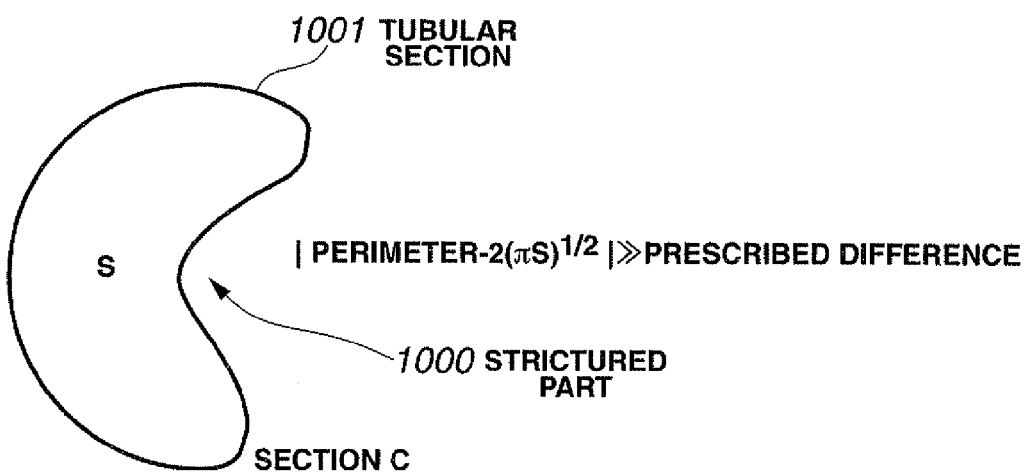
FIG. 36 is a fourth drawing illustrating the processing of FIG. 8 to determine a bronchial area section.
Figure 37:
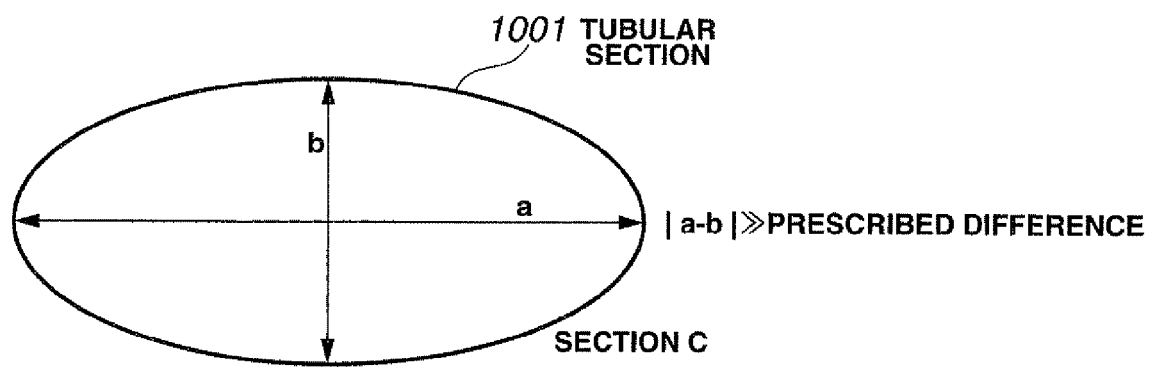
FIG. 37 is a fifth drawing illustrating the processing of FIG. 8 to determine a bronchial area section.
Figure 38:
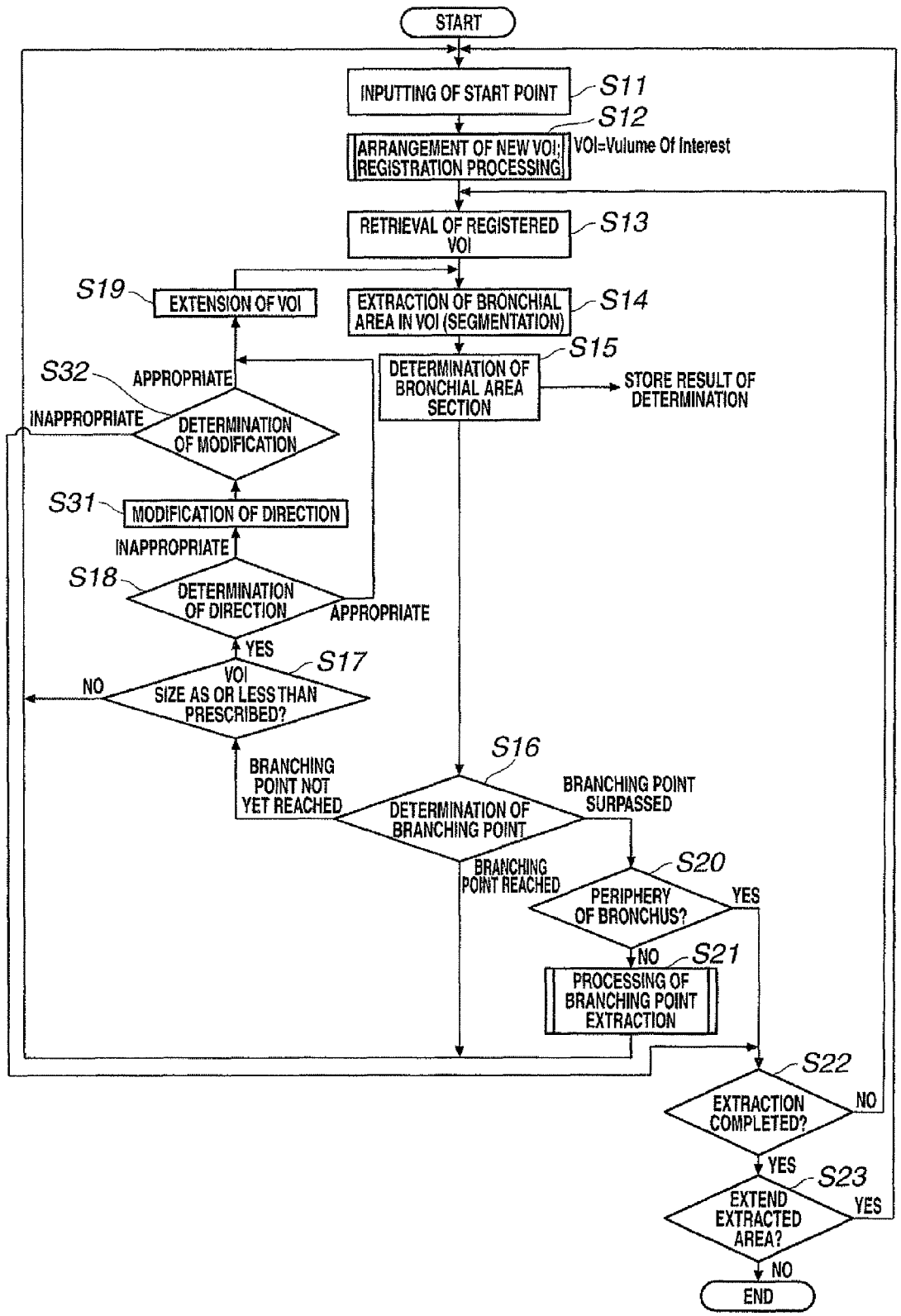
FIG. 38 is a flow chart showing the conventional flow of processing to extract bronchial area information compared with the processing of FIG. 8 to extract bronchial area information.
Figure 39:
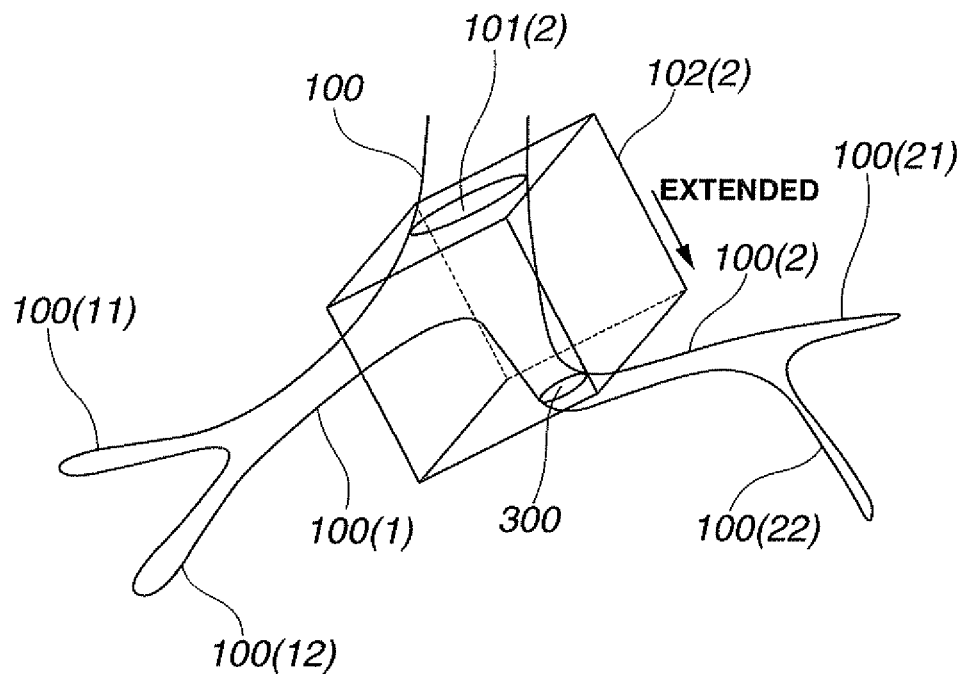
FIG. 39 is a first drawing illustrating the processing of FIG. 38 to extract bronchial area information.

FIG. 31 is a first drawing illustrating the processing of FIG. 8 to extract a branching point; FIG. 32, a second drawing illustrating the processing of FIG. 8 to extract a branching point; FIG. 33, a first drawing illustrating the processing of FIG. 8 to determine a bronchial area section; FIG. 34, a second drawing illustrating the processing of FIG. 8 to determine a bronchial area section; FIG. 35, a third drawing illustrating the processing of FIG. 8 to determine a bronchial area section; FIG. 36, a fourth drawing illustrating the processing of FIG. 8 to determine a bronchial area section; FIG. 37, a fifth drawing illustrating the processing of FIG. 8 to determine a bronchial area section; FIG. 38, a flow chart showing the conventional flow of processing to extract bronchial area information compared with the processing of FIG. 8 to extract bronchial area information; FIG. 39, a first drawing illustrating the processing of FIG. 38 to extract bronchial area information; and FIG. 40, a second drawing illustrating the processing of FIG. 38 to extract bronchial area information.

Figure 41:
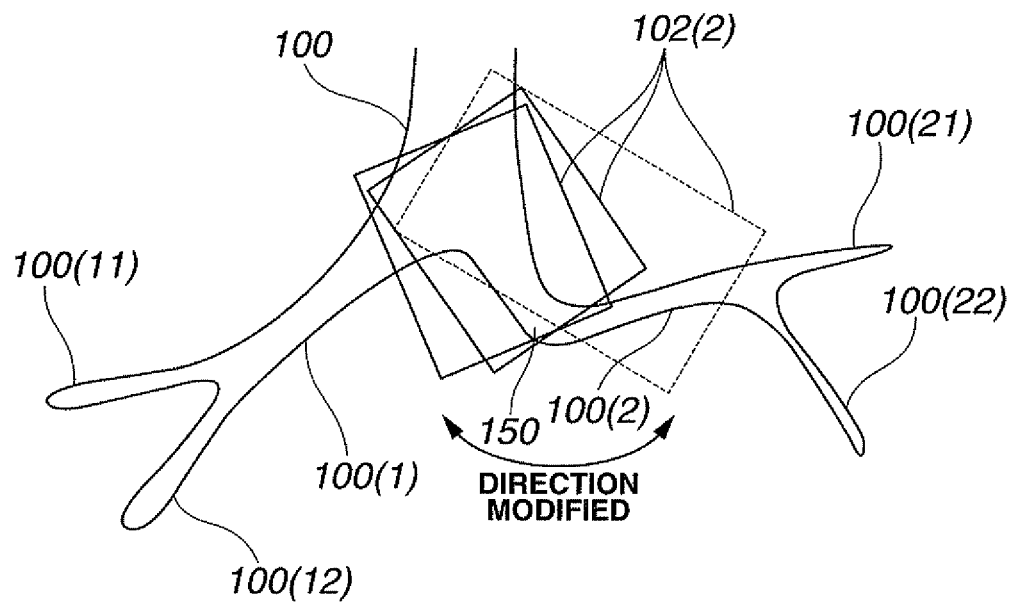
FIG. 41 is a third drawing illustrating the processing of FIG. 38 to extract bronchial area information.
Figure 42:
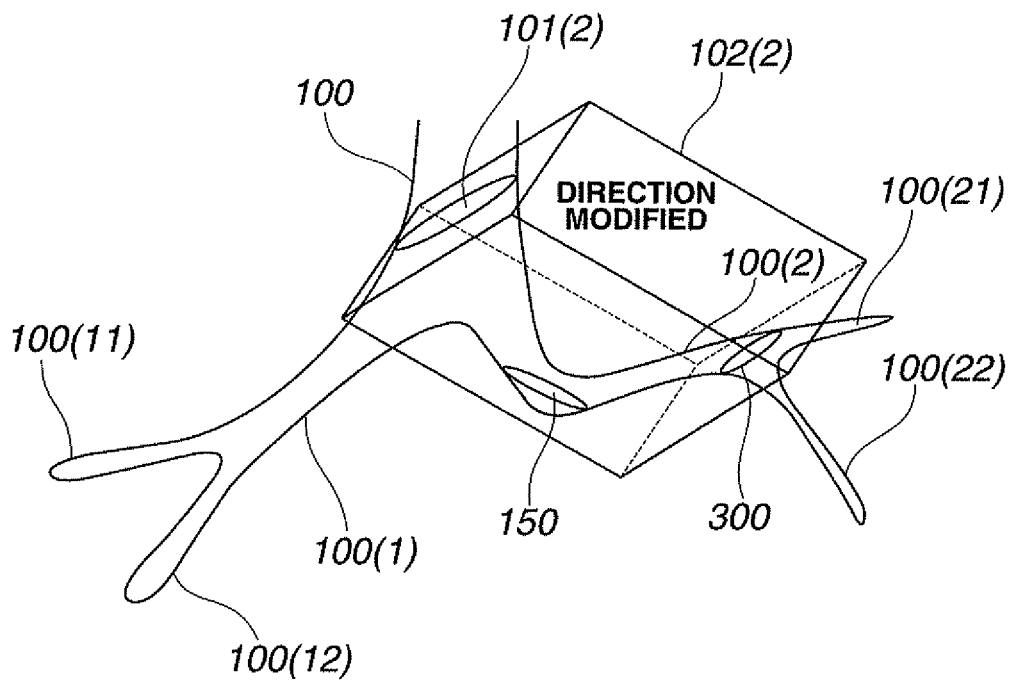
FIG. 42 is a fourth drawing illustrating the processing of FIG. 38 to extract bronchial area information.
Figure 43:
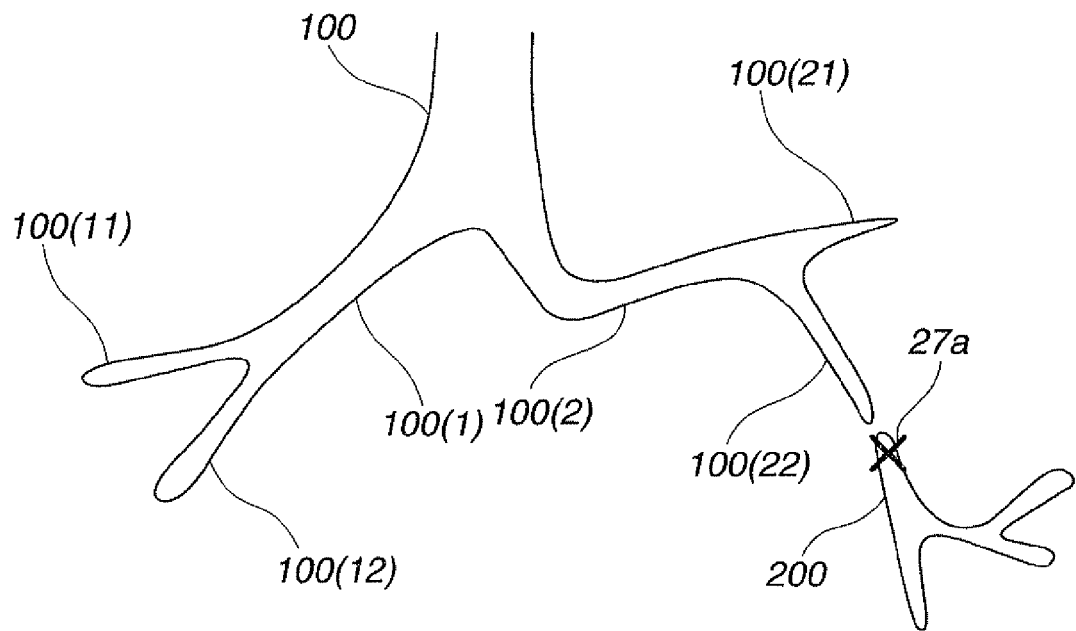
FIG. 43 is an 18th drawing illustrating the processing of FIG. 8 to extract bronchial area information.
Figure 44:
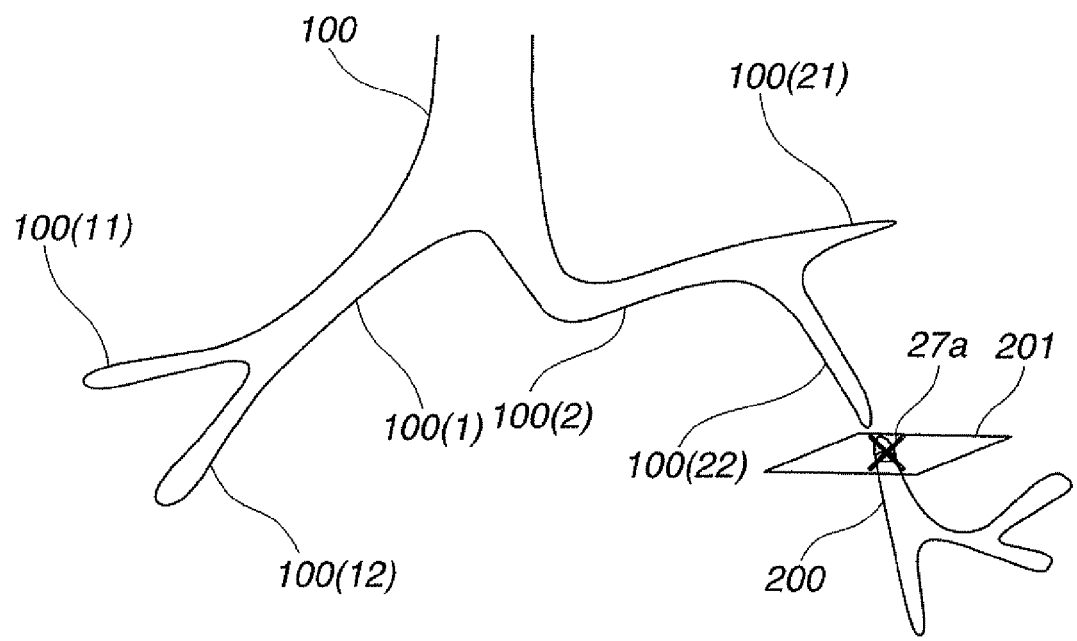
FIG. 44 is a 19th drawing illustrating the processing of FIG. 8 to extract bronchial area information.
Figure 45:
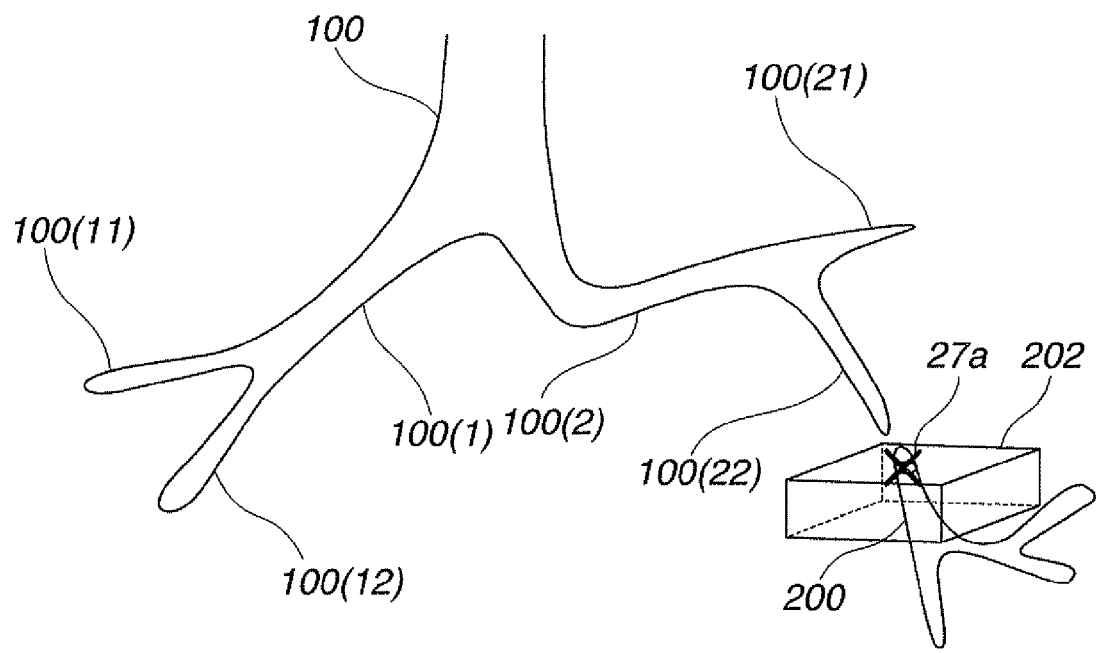
FIG. 45 is a 20th drawing illustrating the processing of FIG. 8 to extract bronchial area information.
Figure 46:
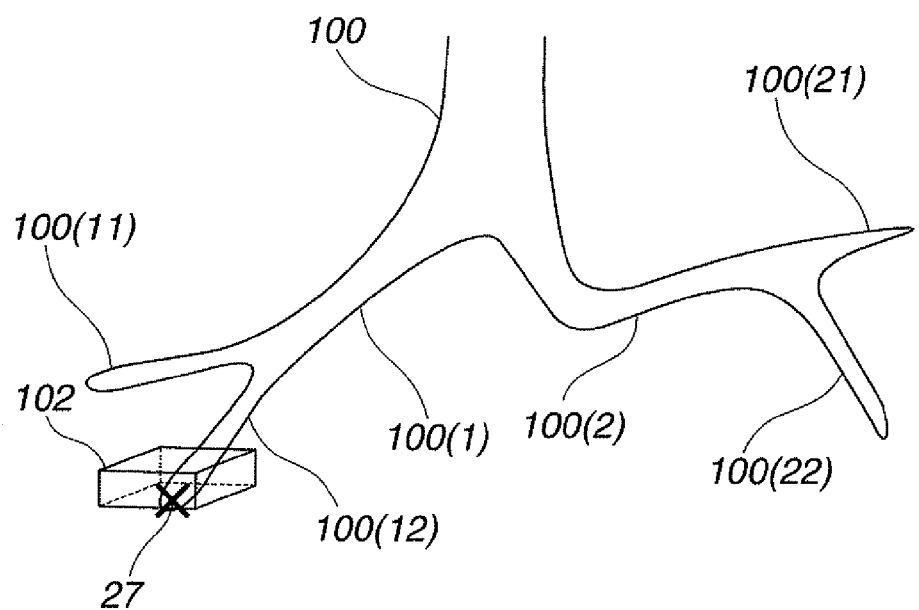
FIG. 46 is a 21st drawing illustrating the processing of FIG. 8 to extract bronchial area information.
Figure 47:
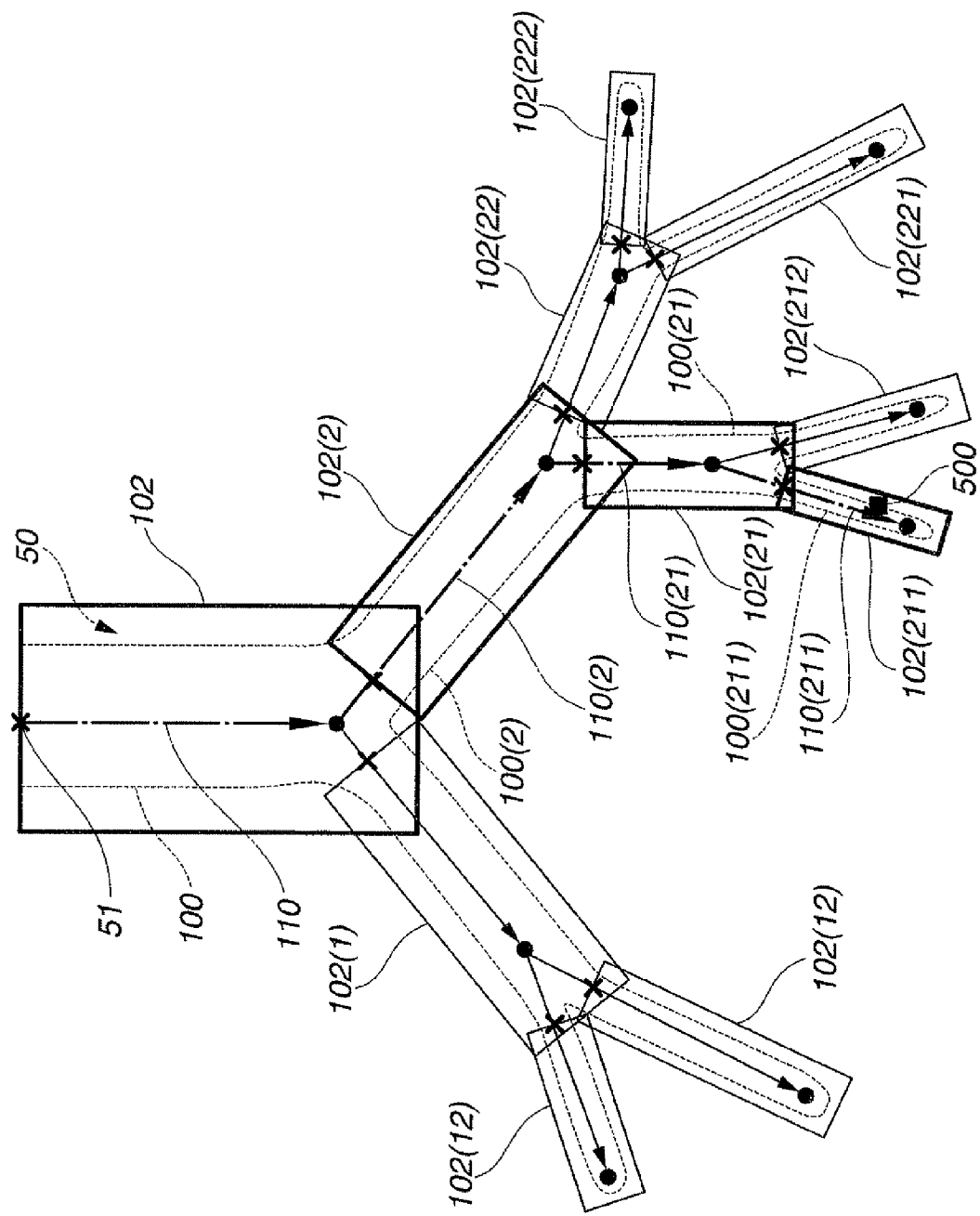
FIG. 47 is a first drawing illustrating route setting by the route setting section of FIG. 1.
Figure 48:
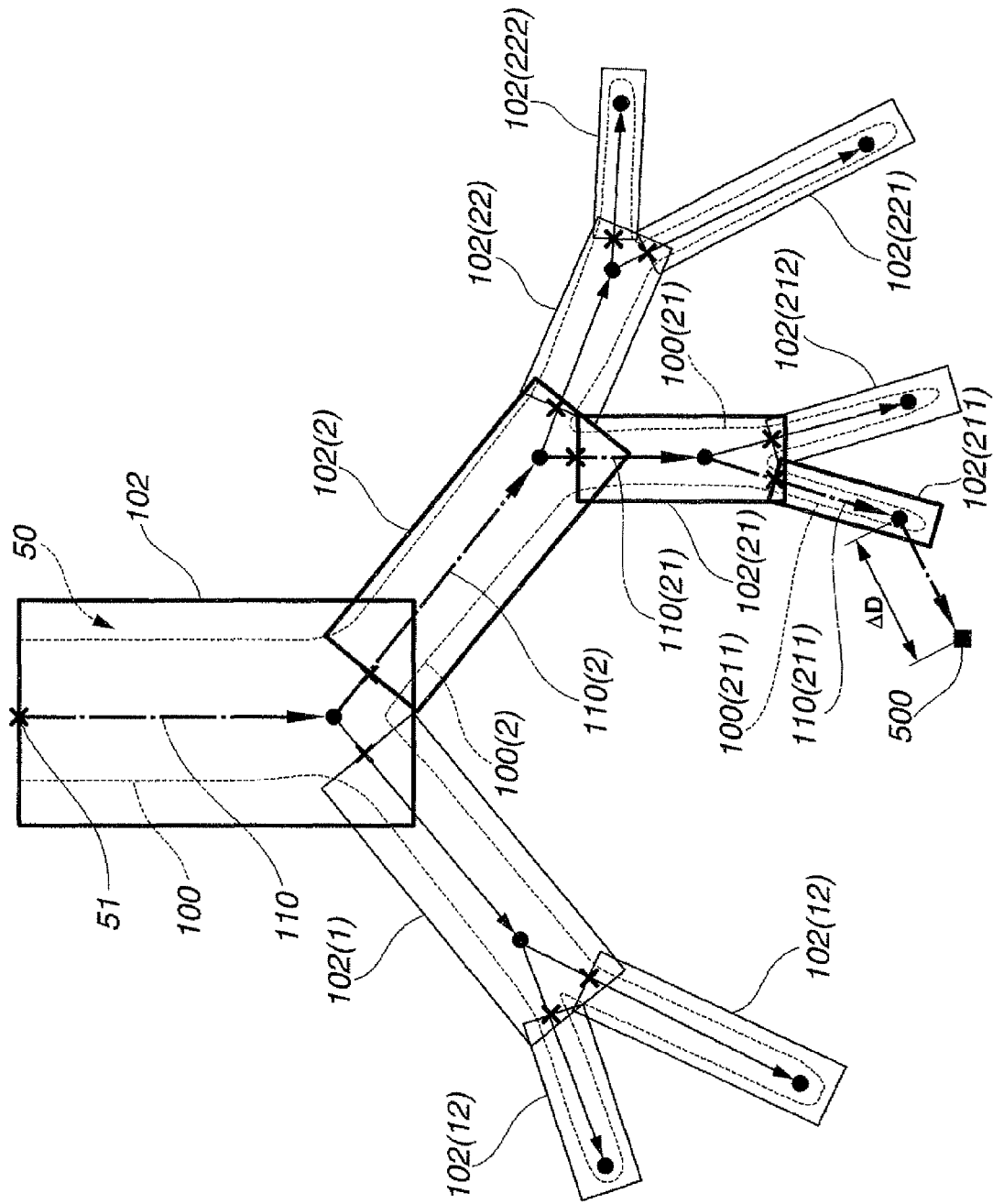
FIG. 48 is a second drawing illustrating route setting by the route setting section of FIG. 1.
Figure 49:
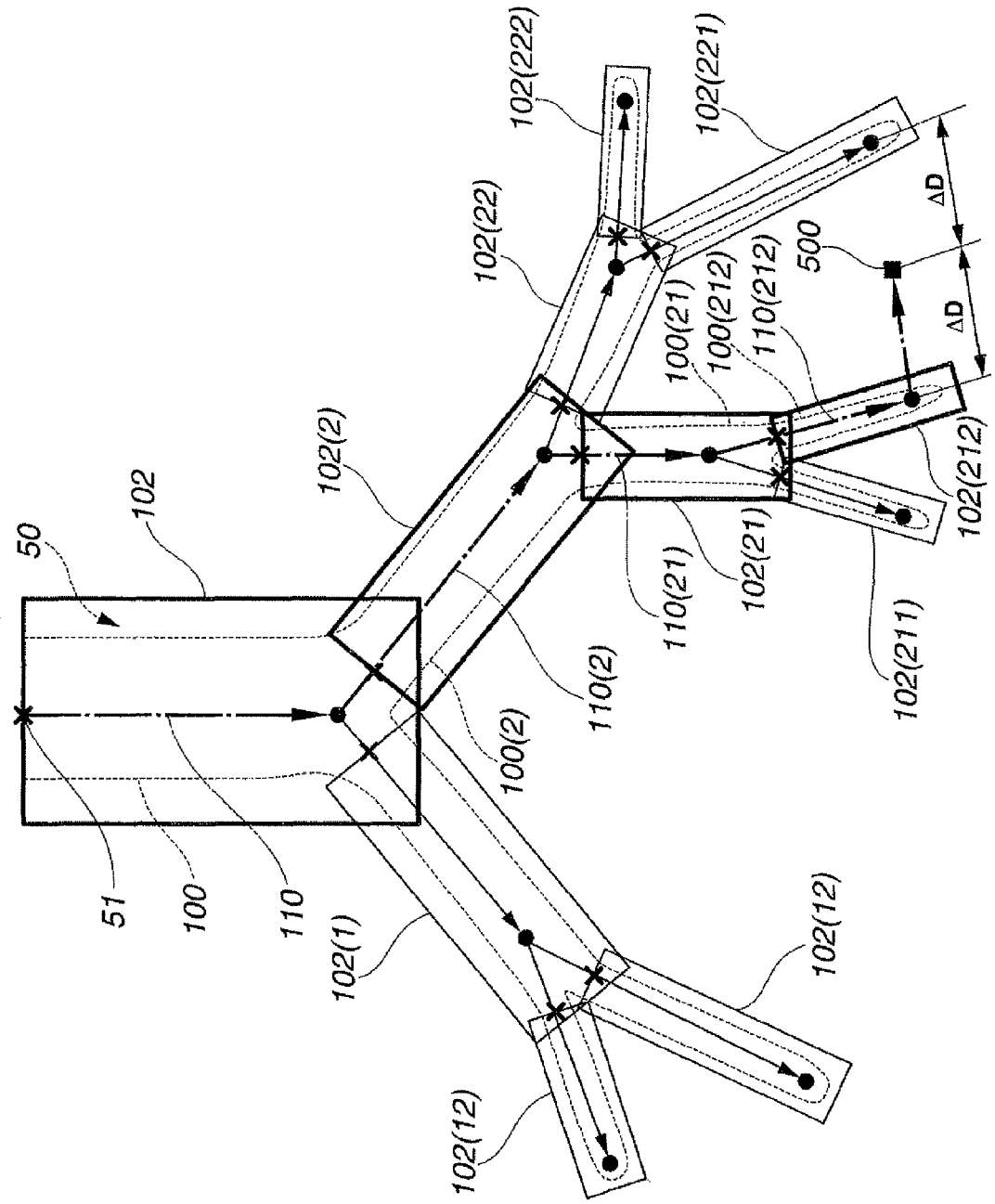
FIG. 49 is a third drawing illustrating route setting by the route setting section of FIG. 1.

FIG. 41 is a third drawing illustrating the processing of FIG. 38 to extract bronchial area information; FIG. 42, a fourth drawing illustrating the processing of FIG. 38 to extract bronchial area information; FIG. 43, an 18th drawing illustrating the processing of FIG. 8 to extract bronchial area information; FIG. 44, a 19th drawing illustrating the processing of FIG. 8 to extract bronchial area information; FIG. 45, a 20th drawing illustrating the processing of FIG. 8 to extract bronchial area information; FIG. 46, a 21st drawing illustrating the processing of FIG. 8 to extract bronchial area information; FIG. 47, a first drawing illustrating route setting by the route setting section of FIG. 1; FIG. 48, a second drawing illustrating route setting by the route setting section of FIG. 1; FIG. 49, a third drawing illustrating route setting by the route setting section of FIG. 1; and FIG. 50, a fourth drawing illustrating route setting by the route setting section of FIG. 1.

Figure 51:
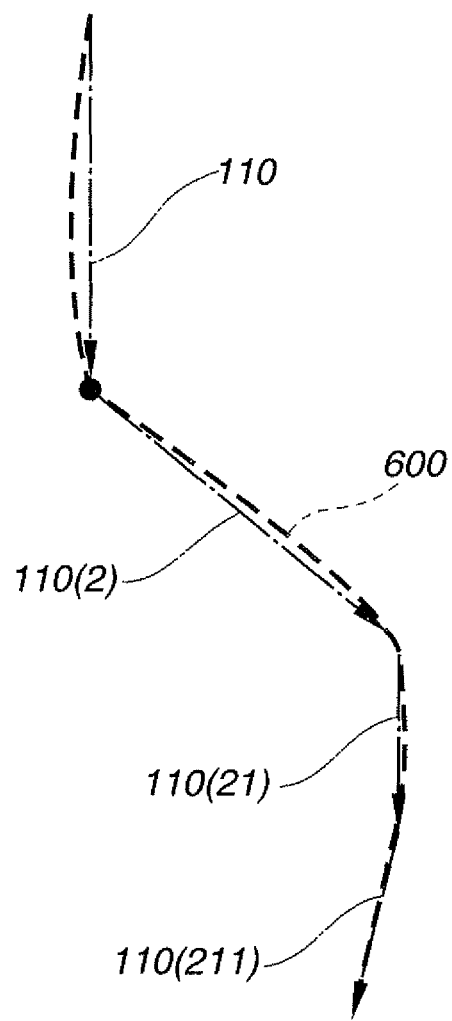
FIG. 51 is a drawing illustrating the processing to bend by the route setting section of FIG. 1.
Figure 52:
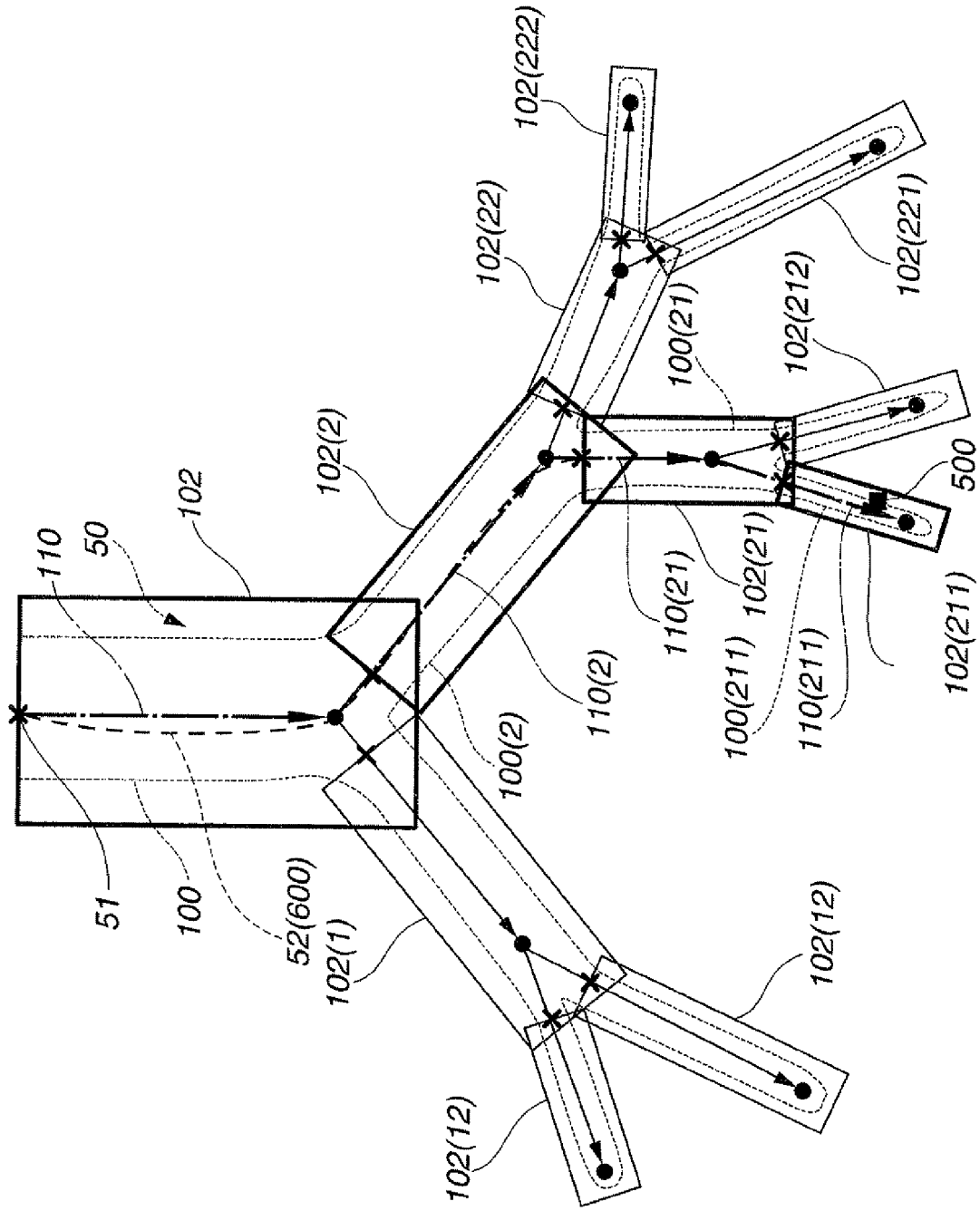
FIG. 52 is a drawing showing the route having undergone the bend processing of FIG. 51.
Figure 53:
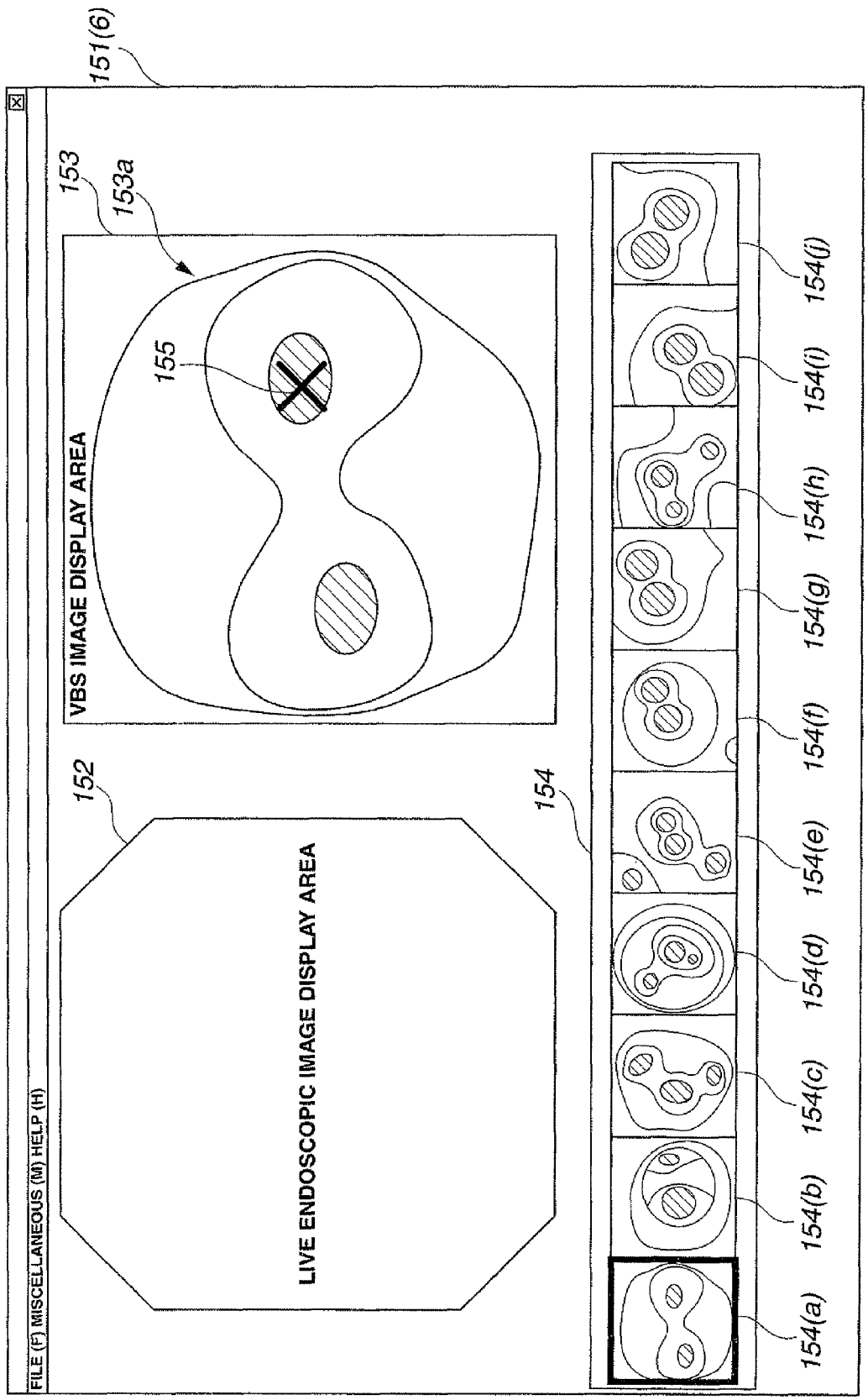
FIG. 53 is a drawing showing an insertion support screen generated by the endoscope insertion support apparatus of FIG. 1.

FIG. 51 is a drawing illustrating the processing to bend by the route setting section of FIG. 1; FIG. 52, a drawing showing the route having undergone the bend processing of FIG. 51; FIG. 53, a drawing showing an insertion support screen generated by the endoscope insertion support apparatus of FIG. 1; and FIG. 54, a drawing showing a modified example of a VOI generated by the VOI generation setting section of FIG. 1.

Embodiment 1

As shown in FIG. 1, a bronchoscope insertion support system 1 as the endoscope insertion support system of the present embodiment comprises a bronchoscope apparatus 2 and an endoscope insertion support apparatus 6 as an apparatus for extracting the bronchial shape.

The endoscope insertion support apparatus 6 extracts the bronchial shape on the basis of CT image data, and generates a virtual endoscopic image of the inside of the bronchus (hereinafter referred to as VBS image). Then, an endoscopic image of the inside of the bronchus obtained by the bronchoscope apparatus 2 (hereinafter referred to as live image) and the VBS image are synthesized to display a synthetic image on a monitor 5 to support insertion of the bronchoscope apparatus 2 into the bronchus.

Further the bronchoscope apparatus 2, though not shown, comprises a bronchoscope having an image pickup section, a light source which supplies illuminating light to the bronchoscope, a camera control unit which subjects image pickup signals from the bronchoscope to signal process, and so forth.

The bronchoscope apparatus 2 then inserts the bronchoscope into the bronchus within the body of a patient and subjects a target tissue to biopsy while picking up images of the inside of the bronchus.

Further, the endoscope insertion support apparatus 6 synthesizes the live image and the VBS image, and also displays a synthetic image on an operational monitor 7. The operational monitor 7 is provided with an input section 8 made up of a touch panel, and it is made possible to easily operate the input section 8 made up of a touch panel while manually inserting the bronchoscope.

The endoscope insertion support apparatus 6 comprises a CT image data capturing section 10, a CT image data storage section 11, an MPR image generating section 12 as a multiplanar reformation image generating section, and a VOI (Volume of Interest; hereinafter referred to simply as VOI) generation setting section 13 as a volume area setting section and a hierarchical volume area setting section, an organ area extracting section 14 as an organ area information calculating section and a heteromorphic state detecting section, a route setting section 15 as a route setting section, a VBS image generating section 16, a VBS image storage section 17, an image processing section 18, an image display control section 19 and a setting information input section 20. Each of the above-stated sections will be described below.

The CT image data capturing section 10 captures three-dimensional image data generated by a known CT apparatus, not shown, for picking up X-ray tomograms of the patient via a portable storage medium such as an MO (Magnetic Optical disk) apparatus or a DVD (Digital Versatile Disk) apparatus, for instance.

The CT image data storage section 11 stores the CT image data captured by the CT image data capturing section 10.

The MPR image generating section 12 generates an MPR image (multiplanar reformation image) on the basis of the CT image data stored in the CT image data storage section 11.

The VOI generation setting section 13 sets a VOI of a prescribed size on the CT image data, including the start point set on the MPR image by the setting information input section 20, stored in the CT image data storage section 11. Incidentally, the VOI generation setting section 13, as will be described afterwards, has a function to extend the set VOI or altering its direction by turning it or to set a new VOI with a new optional position as the initial point. Details will be described later on.

The organ area extracting section 14 extracts tubular path area information (including at least the inner wall face of the tubular path) of the tubular organ from the CT image data in the VOI set by the VOI generation setting section 13 (hereinafter referred to as segmentation processing). Further the organ area extracting section 14 links the tubular path area information obtained by segmentation processing of an organ structure with respect to each of a plurality of VOI set by the VOI generation setting section 13, and executes processing to extract tubular path area information on the whole bronchus. Specific processing by the organ area extracting section 14 will be described afterwards.

The route setting section 15 sets the optimal insertion route for supporting within the bronchus from the start point of support, where insertion support is started by the setting information input section 20, to the target, which is the end point of support, from the tubular path area information on the whole bronchus extracted by the organ area extracting section 14.

The VBS image generating section 16 generates frame by frame consecutive VBS images on the route set by the route setting section 15 on the basis of the CT image data stored in the CT image data storage section 11.

The VBS image storage section 17 stores the VBS images generated by the VBS image generating section 16.

The image processing section 18 inputs image pickup signals from the bronchoscope apparatus 2 and input signals from the input section 8, and generates an endoscope insertion support screen which, to be described afterwards, is a synthetic image comprising the live image, the VBS image and a plurality of thumbnail VBS images.

The image display control section 19 causes a route setting screen generated by the route setting section 15 and the insertion support screen generated by the image processing section 18 to be displayed on the monitor 5.

The setting information input section 20 is made up of a keyboard and a pointing device or the like for inputting setting information to the VOI generation setting section 13 and the route setting section 15.

The bronchoscope apparatus 2 is adapted to receive the VBS image and the thumbnail VBS image from the image processing section 18 of the endoscope insertion support apparatus 6, to display on the operational monitor 7 the insertion support image, which is a synthetic image synthesized with the live image, and to output input information from the input section 8, made up of a touch sensor, of the operational monitor 7 to the image processing section 18 of the endoscope insertion support apparatus 6.

Incidentally, the CT image data storage section 11 and the VBS image storage section 17 may as well be composed of a single hard disk, and the MPR image generating section 12, the VOI generation setting section 13, the organ area extracting section 14, the route setting section 15, a VBS image generating section 16 and the image processing section 18 may be composed of a single arithmetic processing circuit.

The CT image data capturing section 10 is supposed to capture CT image data via a portable storage medium such as an MO or a DVD, but where the CT apparatus or an in-hospital server storing the CT image data is connected to an in-hospital LAN, the CT image data capturing section 10 may as well be composed of an interface circuit connectable to the in-hospital LAN and the CT image data may be captured via the in-hospital LAN. The VOI generation setting section 13, as shown in FIG. 2, comprises a VOI setting function section 13*a* as a setpoint coordinates designating section and a volume area setting section, a VOI extending function section 13*b* as a volume area altering section, a VOI direction determining function section 13*c* as a direction determining section, a VOI branch determining function section 13*d*, a VOI resetting function section 13*e* as a setpoint coordinates designating section and a hierarchical volume area setting section, a VOI information storage function section 13*f*, a VOI size determining function section 13*g* and a VOI branch extracting function section 13*h*. Details of these functional sections will be described afterwards.

Incidentally, the setpoint coordinates designating section is composed of the VOI setting function section 13*a* and the VOI resetting function section 13*e*. The contained state determining section is composed of the VOI direction determining function section 13*c*, the VOI size determining function section 13*g* and the VOI branch extracting function section 13*h*.

The actions of the present embodiment configured in this way will be described.

As shown in FIG. 3, in advance of observation and treatment with the bronchoscope apparatus 2, the endoscope insertion support apparatus 6 at step S1 captures with the CT image data capturing section 10 CT image data of the patient generated by the CT apparatus, and stored at step S2 the captured CT image data into the CT image data storage section 11.

By the operation of the setting information input section 20 at step S3, the VOI generation setting section 13 causes a patient information selecting screen 22 as shown in FIG. 4 to be displayed on the monitor 5 via the image processing section 18 (see FIG. 1), and waits for selection of patient information by the user on the patient information selecting screen 22.

Here, the user selects patient information, and selects a VOI setting button 23 of the patient information selecting screen 22 with a pointer 24 by operating the setting information input section 20. The selection of patient information on the patient information selecting screen 22 is accomplished, for instance, by inputting a patient ID which identifies the patient with the setting information input section 20.

Upon confirmation of the selecting operation by the user, the MPR image generating section 12 at step S4 generates via the image processing section 18 (see FIG. 1) an MPR image composed of, for instance, three selected different multiplanar images of the patient. Thus, the MPR image generating section 12 generates an MPR image 25 composed of an axial image 25*a*, a sagittal image 25*b* and a coronal image 25*c* and an MPR screen 26 having a VOI information screen 28 showing VOI information, and displays the same on the monitor 5 via the image processing section 18 (see FIG. 1).

Then, the endoscope insertion support apparatus 6 at step S5 waits for setting of the start point, which is the set position of a root VOI on the MPR image 25 by the user. Hereupon, when the user, by using the setting information input section 20, designates with the pointer 24 the start point, which is the set position of the root VOI on the MPR image 25, a start point marker 27 is displayed in the designated position on the MPR image 25. Incidentally, this start point is designated within a bronchus running in parallel to the direction of the body axis (the direction linking the head and the feet: a direction orthogonal to the sliced images of the CT image), such as the trachea.

Next, at step S6, in the processing to extract bronchial area information to be described afterwards, the VOI generation setting section 13 sets the root VOI, which is a volume area, at the start point marker 27 and, while a plurality of VOI are being set with the root VOI as the initial point, the organ area extracting section 14 executes intra-VOI segmentation processing. Incidentally, the root VOI is set so as to have a top face normal to the direction of the body axis and containing the start point.

While this processing will be described in detail afterwards, schematically, when the VOI generation setting section 13 designates the start point marker 27 in the position of a desired bronchial tree of a bronchus 50 as shown in FIG. 6, the VOI generation setting section 13 further sets a root VOI 102 of a prescribed size containing the start point marker 27, and the organ area extracting section 14 processes segmentation of the whole bronchus 50 by extending the VOI 102 or resetting a new VOI.

At step S7, the route setting section 15, as shown in FIG. 7, sets a route 52 which extends from an insertion support start point 51, set by the setting information input section 20 on the bronchus 50 displayed on the monitor 5, to a target 500, which is the insertion support end point. When the route 52 is set, the VBS image generating section 16 generates frame by frame consecutive VBS images of the route 52 which has been set.

Incidentally, the insertion support start point 51 does not necessarily coincide with the start point marker 27, and the insertion support start point 51 is set in a position where the user needs the start of the insertion support.

Next at step S8, the VBS image generating section 16 stores the generated VBS image into the VBS image storage section 17, and at step S9 the image processing section 18 and the image display control section 19 make displayable on the monitor 5 and the operational monitor 7 the VBS image stored in the VBS image storage section 16 corresponding to manual insertion of the bronchoscope apparatus 2.

By the processing of steps S1 through S9 described above, preparations for insertion support by the endoscope insertion support apparatus 6 at the time of observation and treatment with a bronchoscope are completed.

Next, details of processing to extract bronchial area information at step 6 above will be described with reference to flow charts of FIG. 8 and FIG. 9.

In the processing to extract bronchial area information, as charted in FIG. 8, the start point (setpoint) is designated at step S11 with the setting information input section 20 by the instruction of the user and, when the start point marker 27 is set at the start point (setpoint), a root VOI 102 is newly arranged and registered at step S12.

Figure 10:
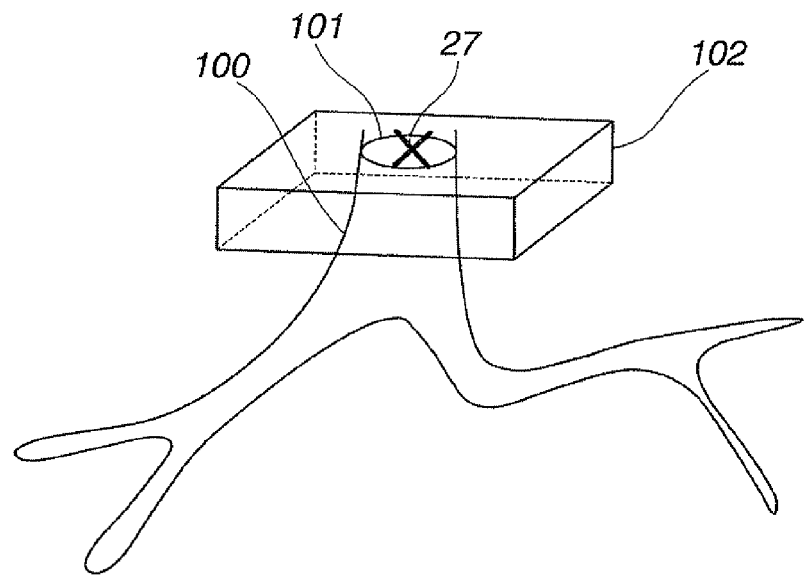
FIG. 10 is a first drawing illustrating the processing of FIG. 8 to extract bronchial area information.

Whereas details of the processing of VOI arrangement and registration at step S12 will be described afterwards, in specific terms here, as shown in FIG. 10, in the VOI generation setting section 13, the VOI setting function section 13a sets the root VOI 102 of a prescribed size in, for instance, a quadrangular prism shape, containing an upper section 101 on which the start point marker 27 of a first layer bronchial tree 100 of the bronchus is set. Then coordinate data of each of the voxels constituting the root VOI 102, which make up setting information on the root VOI 102, are registered/stored in the VOI information storage function section 13f.

Incidentally, as stated above, the root VOI 102 has a top face containing the start point normal to the direction of the body axis, and has a bottom face nearer to the feet than the start point.

Next at step S13, the organ area extracting section 14 takes out coordinate data of each of the voxels of the root VOI 102 registered in the VOI information storage function section 13f. Then at step S14, as shown in FIG. 11, the organ area extracting section 14 extracts tubular path area information on the first layer bronchial tree 100 in the root VOI 102 by executing segmentation processing on the basis of CT image data from the CT image data storage section 11, to the root VOI 102 and stores the tubular path area information into a storage section (not shown) within the organ area extracting section 14.

Then at step S15, the organ area extracting section 14 determines the sectional shape of the bronchial area on the basis of the extracted tubular path area information, and stores the sectional shape into the storage section (not shown) within the organ area extracting section 14. Then at step S16, the VOI branch determining function section 13d determines whether or not the bottom face of the root VOI 102 has reached branching of the bronchial tree.

If it is found not to have reached branching of the bronchial tree, the VOI size determining function section 13g determines at step S17 whether or not the size of the root VOI 102 is as or less than prescribed. Details will be described afterwards.

Next, if the VOI size determining function section 13g determines that the size of the root VOI 102 is as or less than prescribed, the VOI direction determining function section 13c at step S18 determines whether or not the set direction of the root VOI 102 is appropriate relative to a direction 110 in which the first layer bronchial tree 100 extends (hereafter referred to as first layer bronchial tree extending direction).

If it is determined that the direction of the root VOI 102 is appropriate for the first layer bronchial tree extending direction 110, at step S19 the VOI extending function section 13b extends the root VOI 102 by a prescribed quantity Δt in the first layer bronchial tree extending direction 110 and returns to step S14. At step S14, the organ area extracting section 14 executes segmentation processing on the root VOI 102 having been extended by the prescribed quantity Δt on the basis of the CT image data to extract tubular path area information, and stores the sectional shape into the storage section (not shown) within the organ area extracting section 14.

Then the processing of steps S14 through S19 is repeated, and when the extension of the root VOI 102 reaches Δt×n as shown in FIG. 13, at step S16 the VOI branch determining function section 13d detects, for example, branched sections 111(1) and 111(2) of two bronchial trees on the bottom face of the root VOI 102 as shown in FIG. 14, and determines that the first layer bronchial tree 100 has reached branching, the processing returns to step S12. In other words, when the VOI branch determining function section 13d determines at step S16 branching has been reached in the bottom face of the root VOI 102, the processing returns to step S12.

At step S12, as shown in FIG. 15, the VOI resetting function section 13e arranges, using for instance the intersection point between the first layer branch extending direction 110 and the intersection points of the respective gravity centers C1 and C2 of the branched sections 111(1) and 111(2) as a new branching start point (setpoint) b, new VOI 102(1) and VOI 102(2) along the branches as shown in FIG. 16 and FIG. 17. And the VOI resetting function section 13e registers/stores the coordinate data of each of the voxels constituting the VOI 102(1) and the VOI 102(2) into the VOI information storage function section 13f.

These VOI 102(1) and VOI 102(2) constitute hierarchical volume areas relative to the root VOI 102, which is a volume area.

Then in the VOI information storage function section 13f, the coordinate data of each of the voxels constituting the root VOI 102 and the coordinate data of each of the voxels constituting the VOI 102(1) and the VOI 102(2) are linked to form a database and stored. Thus, data are stored in a state in which the coordinate data of each of the voxels constituting the root VOI 102 and the coordinate data of each of the voxels constituting the VOI 102(1) and the VOI 102(2) are linked.

Here, at least the VOI information storage function section 13f registers into a memory not shown which VOI is connected to the coordinates where the top face of the root VOI 102 is located on the three-dimensional data. Also, the VOI information storage function section 13f registers a line segment linking the start point indicated by the start point marker 27 and a branching start point b, a line segment linking the branching start point b and the gravity center C1 and a line segment linking the branching start point b and the gravity center C2 as VOI cores, which are the approximate center lines of the root VOI 102.

Incidentally, the branching start point b is determined by the intersection point of a second layer first branch extending direction 110(1) of a second layer first bronchial tree 100(1) passing the respective gravity centers C1 and C2 of the branched sections 111(1) and 111(2) and having the branched section 111(1) (=the direction in which the second layer first bronchial tree 100(1) extends) and the first layer branch extending direction 110 and the intersection point of a second layer second bronchial tree extending direction 110(2) of a second layer second bronchial tree 100(2) having the branched sections 111(2) (=the direction in which the second layer second bronchial tree 100(2) extends) and the first layer branch extending direction 110.

More specifically, for example, a new VOI 102(1) to be arranged and registered in the second layer first bronchial tree 100(1) is set, as shown in FIG. 16, as a quadrangular prism shape of a prescribed size having the branching start point b on the first layer first bronchial tree 100 and containing on the top face a section 101(1) having as its normal line the second layer first branch extending direction 110(1).

Similarly, a new VOI 102(2) to be arranged and registered in the second layer second bronchial tree 100(2) is set, as shown in FIG. 17, as a quadrangular prism shape of a prescribed size having the branching start point b on the first layer bronchial tree 100 and containing on the top face a section 101(2) having as its normal line the second layer second branch extending direction 110(2).

Also in the new VOI(1) or VOI 102(2) set in this way, the processing of steps S14 through S19 of FIG. 8 described above is repeated.

Thus, to describe the new VOI 102(1) to be arranged and registered in the second layer first bronchial tree 100(1) of FIG. 16 as an example, the organ area extracting section 14 at step S14 executes segmentation extraction processing on the VOI 102(1) on the basis of CT image data from the CT image data storage section 11 to extract tubular path area information on the second layer first bronchial tree 100(1) within the VOI 102(1). And the organ area extracting section 14 stores the tubular path area information into the storage section (not shown) within the organ area extracting section 14.

After step S15, the VOI branch determining function section 13d at step S16 determines whether or not the bottom face of the VOI 102(1) has reached branching of the bronchial tree.

If it is determined not to have reached branching of the bronchial tree, the VOI size determining function section 13g determines at step S17 whether or not the size of the VOI 102(1) is as or less than prescribed. Details will be described afterwards.

Then the VOI direction determining function section 13c at step S18 determines whether or not the set direction of the VOI 102(1) is appropriate relative to the second layer first branch extending direction 110(1).

If it is determined that the direction of the VOI 102(1) is appropriate for the second layer first branch extending direction 110(1), at step S19 as shown in FIG. 18 the VOI extending function section 13b extends the VOI 102(1) by a prescribed quantity in the second layer first branch extending direction 110(1) and returns to step S14; at step S14, the organ area extracting section 14 executes segmentation processing on the VOI 102(1) having been extended by the prescribed quantity on the basis of the CT image data, and the processing of steps S14 through S17 is repeated.

Figure 20:
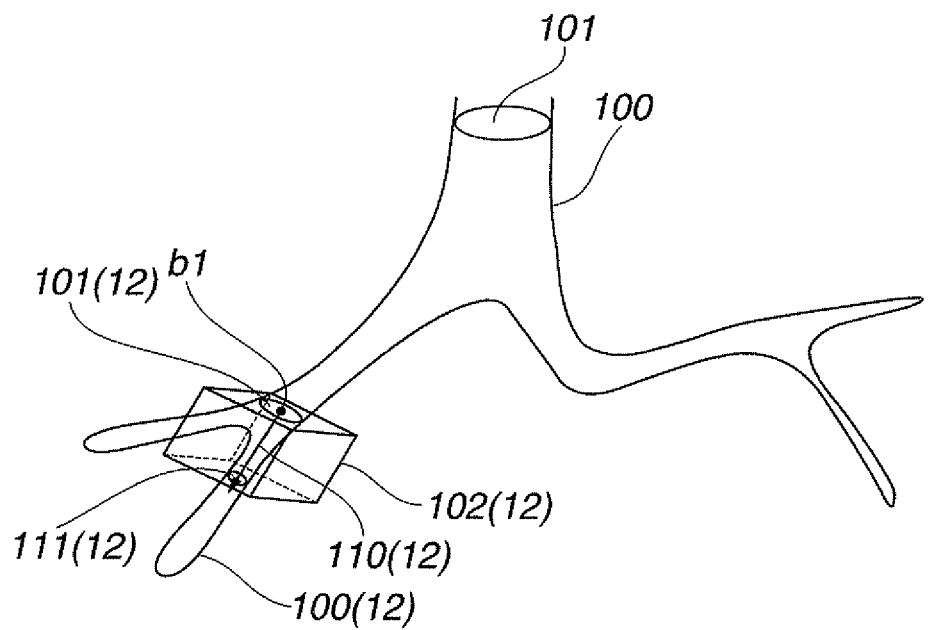
FIG. 20 is an 11th drawing illustrating the processing of FIG. 8 to extract bronchial area information.

If the VOI branch determining function section 13d determines at step S16 the bottom face of the VOI 102(1) has reached branching and the processing returns to step S12, at step S12 the same processing as in the above-described case of arranging the VOI (1) and the VOI 102(2) is performed. Thus, as shown in FIG. 19 and FIG. 20, the VOI resetting function section 13e arranges, using the intersection point between the second layer first branch extending direction 110(1) and the intersection points of respective gravity centers C3 and C4 of branched sections 111(11) and 111(12) as a new branching start point b1, new VOI 102(11) (see FIG. 19) and VOI 102 (12) (see FIG. 20) along the respective branches. And the coordinate data of each of the voxels constituting the VOI 102(11) and the VOI 102(12) are registered/ stored into the VOI information storage function section 13f.

The VOI 102(11) and VOI 102(12) constitute next layer hierarchical volume areas relative to the VOI 102(1), which is a hierarchical volume area.

Then in the VOI information storage function section 13f the coordinate data of each of the voxels constituting the root VOI 102, the coordinate data of each of the voxels constituting the VOI 102(1), and the coordinate data of each of voxels constituting the VOI 102(11) and the VOI 102(12) are linked to form a database and stored.

Here, at least the VOI information storage function section 13f registers into a memory not shown which VOI is connected to the coordinates where the top face of the VOI 102(1) is located on the three-dimensional data. Also, the VOI information storage function section 13f registers a line segment linking a branching start point b in the VOI 102(1) and a branching start point b1 in the VOI 102(11), a line segment linking the branching start point b1 in the VOI 102(11) and the gravity center C3 and a line segment linking the branching start point b1 and the gravity center C2 as VOI cores, which are the approximate center lines of the VOI 102(1).

And at step S13, the organ area extracting section 14 takes out the new VOI 102(11) or the VOI 102(12) registered in the VOI information storage function section 13f, and the above-described processing of steps S14 through S19 of FIG. 8 is repeated.

Thus, to describe the new VOI 102(11) to be arranged and registered in a third layer first bronchial tree 100(11) of FIG. 19 as an example, the organ area extracting section 14 at step S14 executes segmentation extraction processing on the VOI 102(11) on the basis of CT image data from the CT image data storage section 11 to extract tubular path area information on the third layer first bronchial tree 100(11) in the VOI 102(11). And the organ area extracting section 14 stores the tubular path area information into the storage section (not shown) within the organ area extracting section 14.

After step S15, the VOI branch determining function section 13d at step S16 determines whether or not the bottom face of the VOI 102(11) has reached branching of the bronchial tree.

If it is determined not to have reached branching of the bronchial tree, the VOI direction determining function section 13c determines at step S17 whether or not the set direction of the VOI 102(11) is appropriate relative to the third layer first branch extending direction 110(11) (=the direction in which the third layer first bronchial tree 100(11) extends).

If it is determined that the direction of the VOI 102(11) is appropriate for the third layer first branch extending direction 110(11), at step S19 after step S18 the VOI extending function section 13b extends the VOI 102(11) by a prescribed quantity in the third layer first branch extending direction 10(11) as shown in FIG. 21 and returns to step S14; at step S14, the organ area extracting section 14 executes segmentation processing on the VOI 102(11) having been extended by the prescribed quantity on the basis of the CT image data, and the processing of steps S14 through S19 is repeated.

If the VOI branch determining function section 13d determines at step S16 the bottom face of the VOI 102(11) has surpassed the branching point instead of having reached branching, the VOI branch determining function section 13d determines at step S20 whether or not it is a periphery and if it is determined that the periphery has been reached as shown in FIG. 21, the processing advances to step S22 as shown in FIG. 8. If it is determined that the periphery has not been reached, the processing advances to step S21, and at step S21 branching point extraction processing to be described afterwards is executed, followed by a return to step S12.

Incidentally at step S20, if the VOI branch determining function section 13d detects the number of bronchial sections on the bottom face of the VOI 102(11) to be 0 as shown in FIG. 22, it determines that the periphery has been reached.

At step S22, the VOI generation setting section 13 registers/stores the coordinate data of the voxels constituting all the VOI, linked to the VOI information storage function section 13f. The VOI information storage function section 13f registers a line segment linking the branching start point b1 in the VOI 102(11) and a periphery point x1 of the VOI 102(11), as a VOI core of the VOI 102(11).

Further at step S22, the organ area extracting section 14 determines whether or not segmentation processing in the whole bronchial area has been completed on the basis of CT image data and tubular path area information on all the bronchial trees has been stored into the storage section (not shown) within the organ area extracting section 14 (extraction completed).

If the VOI generation setting section 13 and the organ area extracting section 14 determine that the extraction of all the bronchial trees has not been completed, the processing returns to step S13; where any VOI which is registered/stored in the VOI information storage function section 13f and has on its bottom face tubular path area information not extracted is taken out, and the processing of the above-described steps S13 through S22 is executed on the branching of the VOI.

If at step S22 the VOI generation setting section 13 and the organ area extracting section 14 determine that the extraction of all the bronchial trees has been completed, the processing advances to step S23.

At this step S23, whether or not to expand the extraction area of any unextracted bronchial tree is confirmed by the VOI resetting function section 13e according to the user's judgment. If the VOI resetting function section 13e confirms the extraction area of the unextracted bronchial tree, the processing returns to step S11 and extraction from the unextracted bronchial tree is processed. If the VOI resetting function section 13e does not confirm the extraction area of the unextracted bronchial tree, the processing is ended.

Incidentally, details of a specific example of processing at step S23 of judgment on extraction area expansion will be described afterwards.

To describe a new VOI 102(2) to be arranged and registered in the second layer second bronchial tree 100(2) of FIG. 17 as an example, the organ area extracting section 14 at step S14 executes segmentation processing on the VOI 102(2) on the basis of CT image data from the CT image data storage section 11 to extract tubular path area information on the second layer second bronchial tree 100(2) in the VOI 102(2). Then the tubular path area information is stored into the storage section (not shown) within the organ area extracting section 14.

Then at step S16 after step S15, the VOI branch determining function section 13d determines whether or not the bottom face of the VOI 102(2) has reached the branching of the bronchial tree.

If it is determined that the branching of the bronchial tree has not been reached, at step S18 after step S17 the VOI direction determining function section 13c determines whether or not the set direction of the VOI 102(2) is appropriate relative to the second layer second branch extending direction 110(2).

If it is determined that the direction of the VOI 102(2) is appropriate for the second layer second branch extending direction 110(2), at step S19 the VOI extending function section 13b extends the VOI 102(2) by a prescribed quantity in the second layer second branch extending direction 110(2) and returns to step S14; at step S14, the organ area extracting section 14 executes segmentation extraction processing on the VOI 102(2) having been extended by the prescribed quantity on the basis of the CT image data, and the processing of steps S14 through S19 is repeated.

Now during the repetition of the processing of steps S14 through S19, if the second layer second bronchial tree 100(2) is bent on the way beyond a prescribed angle (or curvature) as shown in FIG. 23, a section of the second layer second bronchial tree 100(2) bulges out on a flank besides the bottom face of the VOI 102(2) as shown in FIG. 24 as a result of the extension of VOI 102(2), and the VOI direction determining function section 13c determines at step S18 that the set direction of the VOI 102(2) is inappropriate.

If the direction of the VOI 102(2) is determined to be inappropriate, the VOI extending function section 13b returns the extension of the VOI 102(2) by one step, and positions a section of the second layer second bronchial tree 100(2) only on the bottom face of the VOI 102(2). Then, as shown in FIG. 25, the second layer second bronchial tree 100(2) is split into a plurality of bronchial trees, and the VOI 102(2) having a section of the second layer second bronchial tree 100(2) positioned only on its bottom face is used for extracting tubular path area information of a second layer second bronchial tree 100(2a) of a first level.

Incidentally, as shown in FIG. 26, the upper side of the second layer second bronchial tree 100(2a) of the first level is linked to the first layer bronchial tree 100, and the lower side of the second layer second bronchial tree 100(2a) of the first level is linked to a second layer second bronchial tree 100(2b) of a second level.

Then the processing returns from step S18 to step S12, and the VOI resetting function section 13e at step S12 arranges a new VOI 102(2a) the center of whose upper face is a gravity center g1 of a bronchial section 101(2a) known to be contained in the VOI 102(2) and the center of whose lower face is a gravity center g2 of a bronchial section 101(2a1) known to be contained in the second layer second bronchial tree 100 (2a) of the first level. At step 13, the coordinate data of each of the voxels constituting the VOI 102(2a) are registered/stored into the VOI information storage function section 13f. Then, the processing at and after step S14 is executed.

Incidentally in this processing at step 13 too, the VOI information storage function section 13f links the coordinate data of each of the voxels constituting the root VOI 102, the coordinate data of each of the voxels constituting the VOI 102(2) and the coordinate data of each of the voxels constituting the VOI 102(2a) into a database and stores the data.

Hereupon, the VOI information storage function section 13f at least registers into a memory not shown which VOI is connected to the coordinates where the top face of the VOI 102(2) is located on the three-dimensional data. Also, the VOI information storage function section 13f registers a line segment linking the gravity center g1 in the VOI 102(2) and the gravity center g2 in the VOI 102(2a) as a VOI core of the VOI 102(2a).

The following processing returns from step S16 to step S12 according to the bend of the second layer second bronchial tree 100(2) and, as shown in FIG. 26 for instance, a new VOI 102(2b) to be linked to the VOI 102(2a) is arranged in the second layer second bronchial tree 100(2b) of the second level linked to the second layer second bronchial tree 100(2a) of the first level.

Incidentally, as the criterion by which the VOI direction determining function section 13c determines the direction of a VOI inappropriate, it was stated above that "a section of a bronchial tree bulges out on a flank besides the bottom face", but this is not the only criterion, and if for instance:

(1) "a bronchial tree comes into contact with a flank of a VOI", or, (2) "the gravity center of the bottom face of a VOI does not concur with the gravity center of a bronchial section," the direction of a VOI may be determined to be inappropriate.

Next, with reference to FIG. 9 and FIG. 27 through FIG. 30, the processing to arrange and register a new VOI at step S12 of FIG. 8 will be described.

In the processing to arrange and register a new VOI at step S12 above, as shown in FIG. 9, at step S12a first the VOI setting function section 13a analyzes the sectional shape of a tubular organ in a VOI section, including the setpoint, an extended VOI section extended at step S19, further a section of a new VOI based on the branching point detection at step S16 or a section of a new VOI based on determination of the VOI size at step S17, and a new VOI section based on the determination of the VOI direction at step S18.

Then at step S12b, the VOI setting function section 13a sets a VOI start section having a section 101 of a tubular organ on the basis of the sectional shape of the tubular organ as shown in FIG. 27 for instance.

Next at step S12c, the VOI setting function section 13a calculates the gravity center and the radius r of a section of a tubular organ in the VOI start section on the basis of the sectional shape of the tubular organ, and further the VOI setting function section 13a calculates at step 12d a normal line vector 750 (see FIG. 27) in the direction of the body axis (the axial direction from head to feet) in the section of the tubular organ.

At step S12e, the VOI setting function section 13a sets the VOI 102 (see FIG. 27) as a volume area having on its top face the section 101 of the tubular organ on the basis of the sectional shape of the tubular organ. The size of the VOI 102 is set to, for instance, height=width=a (=5r) and length=b0 (r<b0<a).

Next at step S12f, the VOI setting function section 13a calculates an extension quantity Δt of extension in the direction of the normal line vector 750. Here, Δt is set to be Δt=r, for instance. The Δt (=r) is set to be at least as long as or longer than the length of one pixel of the CT image data.

Further at step S12g, the VOI setting function section 13a stores and registers the coordinates of the VOI start section, the normal line vector 750 and the extension quantity Δt into the storage section (not shown) within the organ area extracting section 14 to complete the processing.

FIG. 28 shows a section of the VOI 102 obtained by slicing the tubular organ shown in FIG. 27 along a plane normal to the VOI start section and parallel to the body axis, while FIG. 29 shows a section of the VOI 102 of FIG. 28 being extended whose size has become, for instance, height=width=a (=5r) and length=b0+4r (>a).

When the VOI 102 becomes b0+4r (>a) in length as shown in FIG. 29, the VOI size determining function section 13g determines at step S17 that the size of the VOI 102 has surpassed a prescribed size. At the step S17, the VOI size determining function section 13g further determines whether or not a difference Δr between the position of the gravity center of the section of the tubular organ on the extended side end face of the extended VOI 102 and the intersection point where the normal line vector 750 crosses on the extended side end face has surpassed a prescribed value L.

If the size of the VOI 102 has surpassed the prescribed size and the difference Δr has surpassed the prescribed value L, the processing returns to step S12, the VOI setting function section 13a links the position of the gravity center of the section of the tubular organ on the extended side end face of the finally extended VOI 102 and the position of the gravity center of the section of the tubular organ on the extended side end face of the VOI 102 one extension step before, and sets a new normal line vector 750' (see FIG. 29) headed in the direction of the body axis (the axial direction from head to feet). Then the VOI setting function section 13a sets as the VOI start section a section of the tubular organ on the extended side end face of the finally extended VOI 102 having a point of orthogonally crossing the normal line vector 750'.

Then the VOI setting function section 13a sets at step S12 a new VOI 102' (see FIG. 29) as a lower layer volume area having a new VOI start section.

Figure 30:
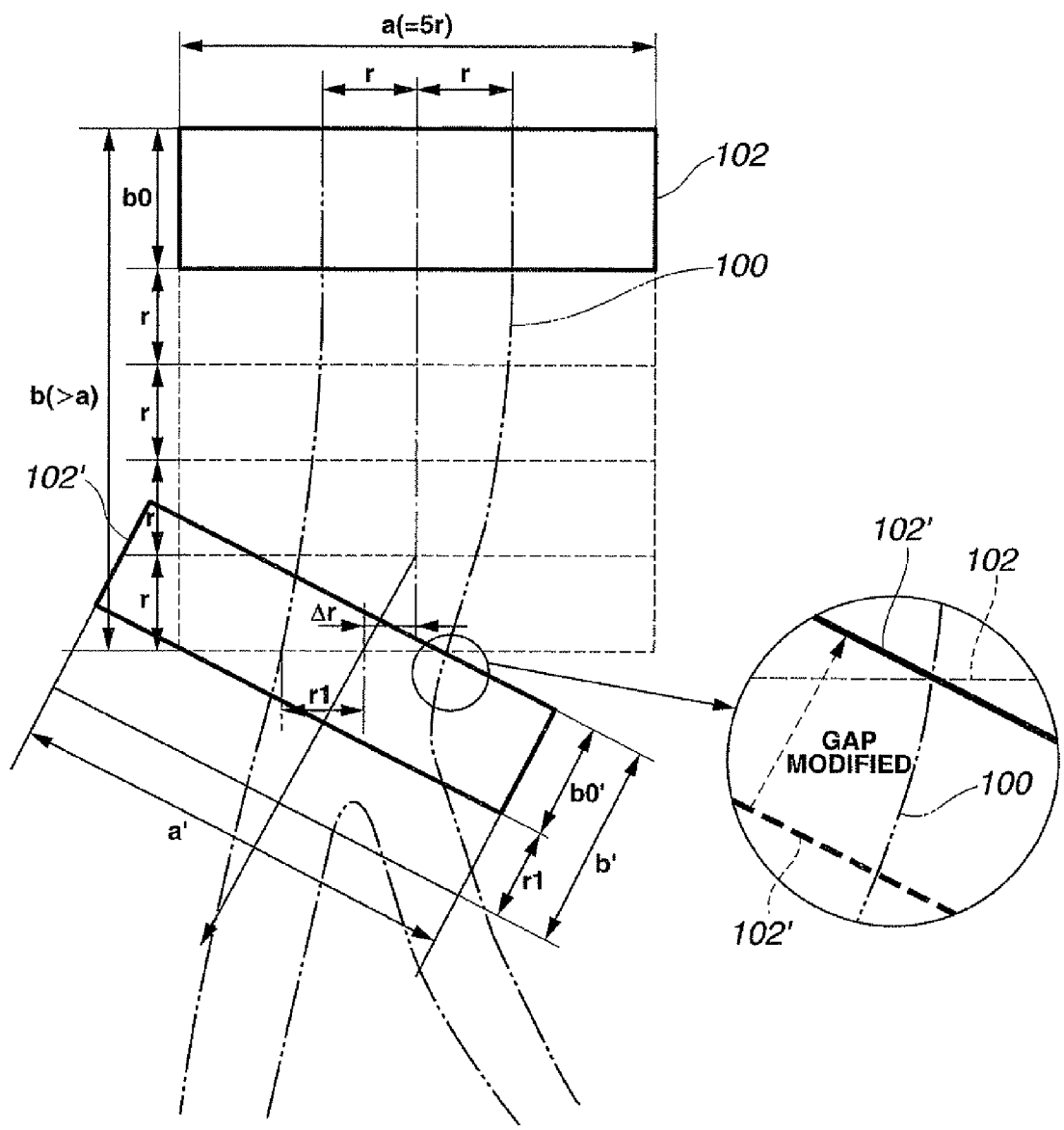
FIG. 30 is a fourth drawing illustrating the processing to arrange and register a new VOI of FIG. 9.

Incidentally, if the VOI start section of the new VOI 102' is simply linked to the gravity center of the final section of the VOI 102, as shown in FIG. 29 a gap may occur between the VOI start section of the new VOI 102' and the final section of the VOI 102, making tubular path area information in the VOI 102 and the new VOI 102' discontinuous to each other. In view of this fear, as shown in FIG. 30, the VOI setting function section 13a corrects the gap so as to keep the continuity of the tubular path area information and sets a new VOI 102' (see FIG. 30).

Previously, the calculation of tubular path area information consumed a very long time as the extension quantity was set pixel by pixel, but the processing to arrange and register a new VOI as described above sets the extension quantity Δt to the radius r of the section of the tubular organ in the VOI start section, which is greater than the conventional pixel-by-pixel extension quantity, enabling tubular path area information to be obtained at high speed.

Incidentally, by setting the extension quantity Δt to the radius r of the section of the tubular organ, in the case of a bronchus, the time taken to acquire tubular path area information on the whole bronchial area can be reduced to ⅙ for instance.

Next, the processing to extract the branching point at step S21 of FIG. 8 will be described with reference to FIG. 31 and FIG. 32. As described with reference to FIG. 8, if it is determined that the branching point is surpassed (step S16) and the bronchial periphery is not reached (step S20), the processing to extract the branching point at step S21 is executed.

In this processing to extract the branching point, as shown in FIG. 31 and FIG. 32, the VOI branch extracting function section 13h advances or retreats in the following procedure the extended side section of the VOI 102 extended at a pitch of r (=Δt) and thereby extracts the branching point (=the point where a branching hole comes into contact).

(1) Set i to 1.

(2) Retreat and shift the extended side section of the VOI 102 by a length of r/(2×i).

(3) Determine whether or not there is a branching point on the extended side section of the shifted VOI 102 and, if there is a branching point, end the processing.

(4-1) If it is determined that there is neither a branching point nor a branching hole on the extended side section of the retreated VOI 102, increment i to extend and shift the extended side section of the VOI 102 by r/(2×1) in length and return to (3) above.

(4-2) If it is determined that there is no branching point on but there is a branching hole in the extended side section of the retreated VOI 102, increment i to retreat and shift the extended side section of the VOI 102 by r/(2×1) in length and return to (3) above.

By repeating the processing of (1) through (4-2) above, though previously it was difficult to converge the extended side section of the VOI 102 onto the position of the branching point, the processing to extract a branching point in the present embodiment enables the extended side section of the VOI 102 to be converged onto the position of the branching point at high speed by a simple procedure.

Next, sectional processing of the bronchial area by the organ area extracting section 14 at step S15 of FIG. 8, which is a characteristic part of the first embodiment, will be described with reference to FIG. 33 through FIG. 37.

As shown in FIG. 33, in the sectional processing of the bronchial area, the organ area extracting section 14 extracts the shape of the extended side section of the VOI 102, and determines whether or not there is a strictured part 1000, for instance, on the extended side section of the VOI 102.

Thus, if there is no strictured part 1000, the extended side section of the VOI 102 is substantially circular as shown in FIG. 34. In this case, in the sectional processing of the bronchial area, the organ area extracting section 14 stores into the storage section (not shown) within the organ area extracting section 14 the radius of the extended side section as $r=(S/\pi)^{1/2}$ because the difference between the circumferential length ($=2\times(\pi S)^{1/2}$) of a true circle matching the area S of the extended side section and the circumferential length of the extended side section is negligible.

Where the deformation quantity in the strictured part 1000 is small, the extended side section of the VOI 102 is a deformed circle as shown in FIG. 35. In this case, in the sectional processing of the bronchial area, the organ area extracting section 14 stores into the storage section (not shown) within the organ area extracting section 14 the radius of the extended side section as $r (S/\pi)^{1/2}$ because the difference between the circumferential length ($=2\times(\pi S)^{1/2}$) of a true circle matching the area S of the extended side section and the circumferential length of the extended side section is not greater than a prescribed difference.

Further, where the deformation quantity in the strictured part 1000 is large, the extended side section of the VOI 102 manifests a shape which cannot be regarded as a circle as shown in FIG. 36. In this case, in the sectional processing of the bronchial area, the organ area extracting section 14 stores into the storage section (not shown) within the organ area extracting section 14 the extended side section as strictured part information because the difference between the circumferential length ($=2\times(\pi S)^{1/2}$) of a true circle matching the area S of the extended side section and the circumferential length of the extended side section is greater than the prescribed difference.

Thus, the organ area extracting section 14 constituting the heteromorphic state detecting section stores into the storage section (not shown) within the organ area extracting section 14 the strictured part information as information indicating the heteromorphic state of the sectional shape of the bronchus.

Incidentally, where the extended side section of the VOI 102 has a substantially oval shape as shown in FIG. 37, in the sectional processing of the bronchial area, the organ area extracting section 14 stores into the storage section (not shown) within the organ area extracting section 14 the extended side section as strictured part information if the difference between a longer axis length a and a shorter axis length b of the extended side section is greater than a prescribed difference. If the difference between the longer axis length a and the shorter axis length b of the extended side section is not greater than the prescribed difference, the organ area extracting section 14 stores into the storage section (not shown) within the organ area extracting section 14 the radius of the extended side section as $r=(S/\pi)^{1/2}$ where S is the square measure of the extended side section having a substantially oval shape.

Incidentally, if it is determined that the section is made heteromorphic, deviating from a true circle, otherwise than by the strictured part 1000, for instance by a polyp-like tissue, the organ area extracting section 14 which is the heteromorphic state detecting section stores information indicating the heteromorphic state into the storage section (not shown) within the organ area extracting section 14.

Incidentally, when a section having information indicating the heteromorphic state of the sectional shape of the bronchus resulting from extending of the VOI as stated above, such as a section having strictured part information for instance, is made a new VOI set section by the VOI resetting function section 13*e*, the VOI resetting function section 13*e* determines and sets the size of a new VOI by using the radius ($r=(S/\pi)^{1/2}$) of the extended side section where the sectional shape of the bronchus immediately before the extension is not in a heteromorphic state.

Regarding the processing to extract bronchial area information with a conventional VOI, for instance in T. Kitasaka, K. Mori, J. Hasegawa and J. Toriwaki: "A Method for Extraction of Bronchus Regions from 3D Chest X-ray CT Image by Analyzing Structural Features of the Bronchus", Form a 17, pp. 321-338 (2002) as Document 2, the processing until steps S11 through S17 is the same as in the present embodiment, but the processing that is performed when the direction of the VOI is determined to be inappropriate in the processing to determine the direction at step S18 is different.

Figure 40:
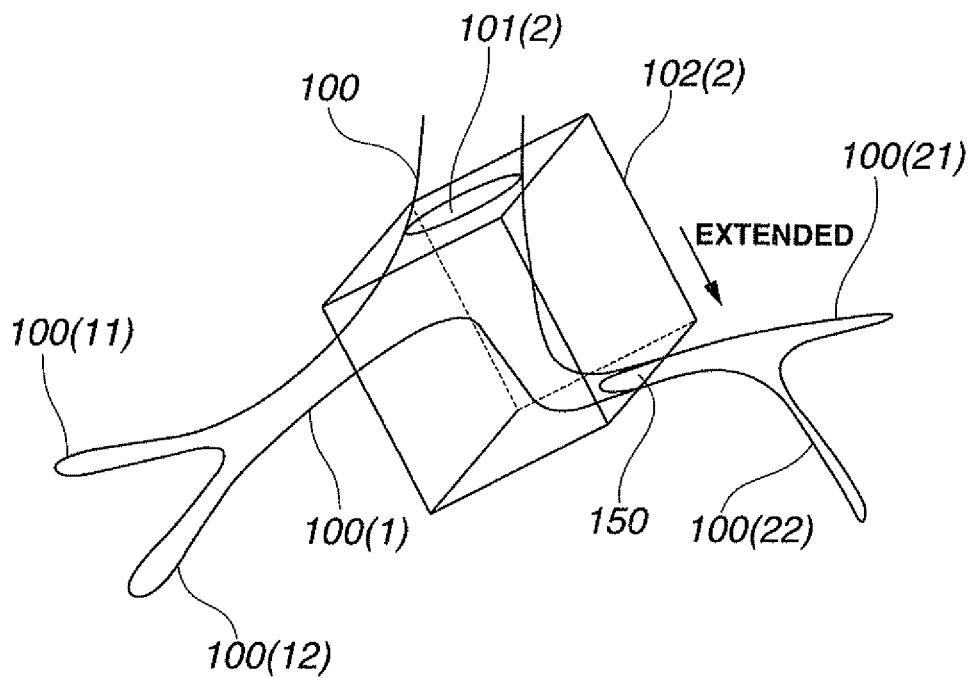
FIG. 40 is a second drawing illustrating the processing of FIG. 38 to extract bronchial area information.

More specifically, as shown in FIG. 39, for instance, when the VOI extending function section 13*b* extracts tubular path area information on the second layer second bronchial tree 100(2) while extending the VOI 102(2), if a flank of the second layer second bronchial tree 100(2) comes into contact with the VOI 102(2) as shown in FIG. 40 as a result of extending the VOI 102(2), the VOI direction determining function section 13*c* determines the direction of the VOI to be inappropriate in the processing to determine the direction at step S16.

In such a case, conventionally the VOI generation setting section 13 would correct the direction of the VOI 102(2) so as to let the second layer second bronchial tree 100(2) enter the VOI 102(2) at step S32 as shown in FIG. 41. However, there may arise a case in which the second layer second bronchial tree 100(2) cannot be accommodated into the VOI 102(2) as shown in FIG. 42.

When the direction of the VOI 102(2) is corrected and the VOI generation setting section 13 determines at step S33 that the second layer second bronchial tree 100(2) can be accommodated into the VOI 102(2), extends the VOI 102(2) at step S19, and returns to step S14 to repeat the processing.

However, if the VOI generation setting section 13 determines at step S32 that the second layer second bronchial tree 100(2) cannot be accommodated into the VOI 102(2), it advances to step S22 and shifts to determination of the completion of extraction. Then if at step S22 the VOI generation setting section 13 and the organ area extracting section 14 determine that the extraction of the whole bronchus has been completed, they complete the processing after step S23 or, if they determine that the extraction of the whole bronchial tree has not been completed, they return to step S13 to repeat the processing.

In the conventional practice as described above, once the direction of the VOI is altered and it is determined that the bronchial tree cannot be accommodated into the VOI, organ area information on that bronchial tree is not extracted.

In such a case, a new VOI 102(2b) to be linked to the VOI 102(2a) is arranged in the second layer second bronchial tree 100(2b) of the second level in the present embodiment as shown in FIG. 26, and the organ area extracting section 14 extracts tubular path area information by using the VOI 102 (2b). Therefore, the present embodiment can securely extract all the consecutive bronchial trees.

Further in the present embodiment, in the processing of judgment on extraction area expansion at step S23 in FIG. 8, where a third layer second bronchial tree 100(22) is not a periphery but is blocked as shown in FIG. 43 for instance, there further is a bronchial tree 200 beyond the blocked end of the third layer second bronchial tree 100(22). Then at step S23 the VOI resetting function section 13e confirms according to the user's judgment whether or not the extraction area is to be expanded to the unextracted bronchial tree 200 beyond the blocked end. When the VOI resetting function section 13e confirms the extraction area of the bronchus 200 beyond the blocked end, the processing returns to step S11.

Then at step S11, the setting information input section 20 designates a start point in the bronchus 200 beyond the blocked end with the instruction of the user, and a start point marker 27a is set. This results in setting of an upper face 201 having the start point marker 27a and containing a section of the bronchus 200 beyond the blocked end at step S12 as shown in FIG. 44 and, further a new VOI 202 having the bronchus 200 beyond the blocked end built into it is arranged and registered as shown in FIG. 45. Then the processing at and after step S13 subjects the bronchus 200 beyond the blocked end to extraction processing.

Incidentally, the start point (setpoint) may as well be set at the periphery of the bronchus as shown in FIG. 46, instead of the proximal end side of the bronchus, to have the VOI arranged and registered from the peripheral side toward the upper part of the body axis to perform extraction processing on the bronchus 200.

Also in the present embodiment, as stated above, a VOI is arranged and registered for every bronchial tree from the start point to the periphery, and a VOI core, which is the approximate center line, is registered with every VOI 102.

Then, upon completion of the extraction of tubular path area information from the whole bronchus from the start point to the periphery, the route setting section 15 sets the route 52 from the support start point 51, set by the setting information input section 20, to the target 500, which is the support end point, on the bronchus 50 displayed on the monitor 5 at step S7 in FIG. 3.

More specifically, as shown in FIG. 47, when the target 500 is designated within the bronchus, a VOI having a VOI core on which the target 500 is located is selected. Referring to FIG. 47, first a VOI 102(211) is selected as the target VOI, a VOI 102(21), a VOI 102(2) and a VOI 102 linked successively to the VOI 102(211) are automatically extracted, and VOI cores 110(211), 110(21), 110(2) and 110 of these VOI 102(211), VOI 102(21), VOI 102(2) and VOI 102 are set by the route setting section 15 as the route 52 from the support start point 51 to the target 500, which is the support end point.

Also, as shown in FIG. 48, when the target 500 is designated outside the bronchus, a plurality of VOIs having VOI cores at the nearest distance ΔD to the target 500 are selected as the target VOI. Referring to FIG. 48, first the VOI 102(211) is selected, and a VOI 102(21), a VOI 102(2) and a VOI 102 linked successively to the VOI 102(211) are automatically extracted, and VOI cores 110(211), 110(21), 110(2) and 110 of these VOI 102(211), VOI 102(21), VOI 102(2) and VOI 102 are set by the route setting section 15 as the route 52 from the support start point 51 to the target 500, which is the support end point.

Figure 50:
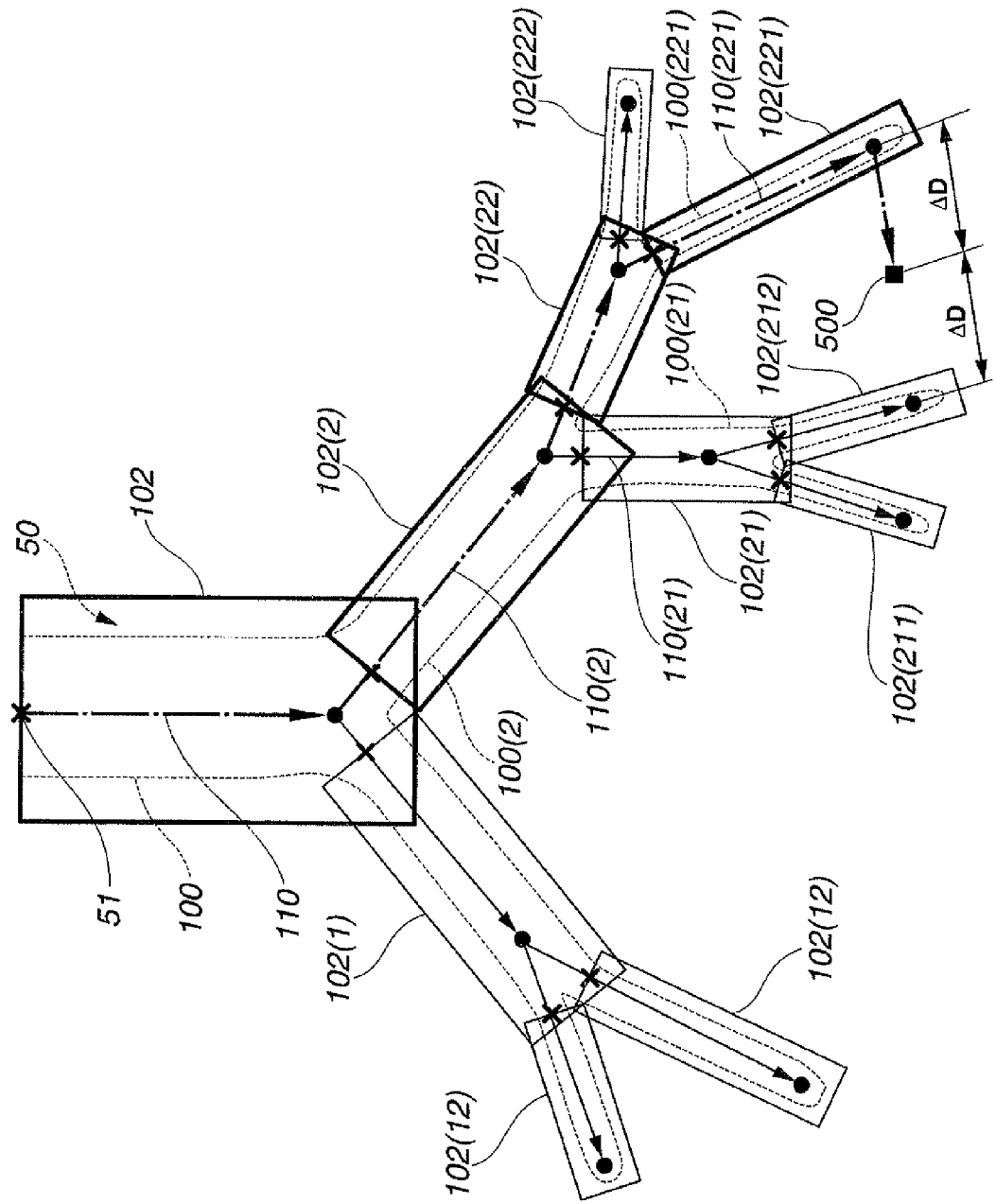
FIG. 50 is a fourth drawing illustrating route setting by the route setting section of FIG. 1.

As shown in FIG. 49 and FIG. 50, when the target 500 is designated outside the bronchus, a plurality of VOIs having VOI cores at the nearest distance ΔD to the target 500 are selected. Referring to FIG. 49, first the VOI 102(212) is selected as the target VOI, and a VOI 102(21), a VOI 102(2) and a VOI 102 linked successively to this VOI 102(212) are automatically extracted. On the other hand, with reference to FIG. 50, first a VOI 102(221) is selected as the target VOI, and a VOI 102(22), a VOI 102(2) and a VOI 102 linked successively to the VOI 102 (221) are automatically extracted.

In the cases illustrated in the FIG. 49 and FIG. 50, the route setting section 15 sets the one shorter in the distance of the cores linked from the support start point 51 to the target 500, which is the support end point, as the route 52. In the cases of FIG. 49 and FIG. 50, the VOI cores 110(212), 110(21), 110(2) and 110 of the VOI 102(212), VOI 102(21), VOI 102(2) and VOI 102 of FIG. 49, which are shorter in the distance of the linked cores, are selected by the route setting section 15 as the route 52 from the support start point 51 to the target 500, which is the support end point.

Further the route setting section 15, after setting the cores linked from the support start point 51 to the target 500, which is the support end point, as the route 52 as described above, executes spline interpolation processing so as to be suitable for observation as shown in FIG. 51 for fine adjustment of each point, correct the route into a smooth curve 600 and, as shown in FIG. 52, sets this curve 600 as the route 52.

In order to simplify the description of an insertion support screen for use in insertion support at the time of observation and treatment with the endoscope insertion support apparatus 6 and the bronchoscope apparatus 2 wherein route setting has been done in this way, a case in which there are 10 branching points on the route will be taken up as example for description.

When bronchoscopy under insertion support with the endoscope insertion support apparatus 6 is started, an insertion support screen 151 as shown in FIG. 53 is displayed on the monitor 5.

The insertion support screen 151 comprises a live endoscopic image display area 152 for displaying a live image 152a from the bronchoscope apparatus 2, a VBS image display area 153 for displaying a VBS image 153a, and branch thumbnail VBS image areas 154 for displaying branch thumbnail VBS images 154(a) through 154(j) obtained by compressing VBS images 153a at all the branching points on the route; the VBS image 153a of the first branching point on the route is displayed on the VBS image display area 153, and the branch thumbnail VBS images 154(a) through 154(j) at all the branching points are displayed on the branch thumbnail VBS image areas 154.

Incidentally, a navi-marker 155 is displayed on the VBS image 153a superposed over a route hole leading to the route. The frame of the same branch thumbnail VBS image as the VBS image 153a displayed in the VBS image display area 153 is displayed in bold lines or in color to make it distinguishable from other thumbnail VBS images, and the operator can readily distinguish it from any other branch thumbnail VBS image. At the initial stage, the frame of the branch thumbnail VBS image 154(a) is displayed in bold lines or in color.

In this way, in the present embodiment a new VOI is set for each branching point after the setting of the root VOI, and a new VOI is also set when it is determined that VOI extension processing has made VOI unable to accommodate any more bronchial tree. Furthermore, when any bronchial tree is strictured or blocked, sectional information on the strictured part is eliminated or corrected to set a new VOI in an appropriate size, and at the same time a new VOI can be set in an appropriate size beyond a blocked bronchial tree. Moreover, as a VOI set in an appropriate size is extended and segmentation processing is executed, tubular path area information can be surely extracted from every bronchial tree at least without affecting by any strictured part.

Further, in setting the route for insertion support, since the target VOI nearest the target 500, which is the support end point, or having the target 500 is selected and the VOI cores leading to the support start point 51 by tracing VOI linked to the target VOI are set as the route, route setting can be accomplished easily and at high speed.

Incidentally, though a VOI is supposed to be shaped as a quadrangular prism in the foregoing description, this is not the only usable shape, but it may be columnar-shaped as shown in FIG. 54 or shaped as a multi-angled pillar whose sectional shape can contain sections of the bronchus in its upper and lower planes.

Although the bronchoscope insertion support system 1 is referred to as the body cavity insertion support system in describing the present embodiment, the present embodiment can be applied to a large intestinal insertion support system or the like, which supports insertion into a complexly bent body cavity organ such as the large intestine, enabling VOI to be appropriately set.

Further, the present embodiment can obviously be applied not only to the bronchus or the large intestine but also to any body cavity organ having a tree structure, such as the blood vessel, small intestine, bile duct, pancreatic duct or lymphatic vessel.

To add, while the conventional practice was to set the quantity of extension pixel by pixel and this required a long time to calculate tubular path area information, a tubular path insertion support system according to an exemplary embodiment of the present invention can obtain tubular path area information at high speed because the processing of new VOI arrangement and registration described above uses the radius r of the section of the tubular organ in the VOI start section as the quantity of extension Δt, which is larger than the conventional pixel-by-pixel quantity of extension (supporting drawings: FIG. 27 through FIG. 30).

Furthermore, while it was difficult by the conventional practice to converge the extended side section of the VOI 102 onto the position of the branching point, the processing to extract a branching point in a tubular path insertion system according to an exemplary embodiment of the present invention enables the extended side section of the VOI 102 to be converged onto the position of the branching point at high speed by a simple procedure (supporting drawings: FIG. 31 and FIG. 32).

The present invention is not limited to the present embodiment described above, but can be altered or modified in various ways without deviating from the essentials of the invention.

What is claimed is:

1. An endoscope insertion support system comprising:
    a volume area setting processing circuit for setting a volume area which has a start point set in a tubular path of a tubular organ within three-dimensional image data of a subject and has a size so prescribed as to contain the tubular organ;
    an organ area information calculating processing circuit which extracts tubular area information in the volume area on the basis of the three-dimensional image data of the tubular organ in the volume area and calculates segmentation data representing a tubular path shape;
    a contained state determining processing circuit which determines whether or not the tubular path is contained in the volume area set by the volume area setting processing circuit;
    a heteromorphic state detecting processing circuit which detects a strictured or expanded state of the tubular path, as a heteromorphic state, on the basis of at least one of a diameter, area and circumferential length out of the segmentation data calculated by the organ area information calculating processing circuit; and
    a hierarchical volume area setting processing circuit which sets a hierarchical volume area obtained by being hierarchically arranged and linked to the volume area set by the volume area setting processing circuit to a size based on a result of determination by the contained state determining processing circuit.

2. The endoscope insertion support system according to claim 1, wherein:
    the hierarchical volume area setting processing circuit sets a next-step hierarchical volume area which further hierarchically links to the hierarchical volume area;
    the organ area information calculating processing circuit calculates segmentation data representing a tubular path shape in the next-step hierarchical volume area;
    the heteromorphic state detecting processing circuit detects heteromorphic state of the tubular path shape in the hierarchical volume area on the basis of a result of calculation of the organ area information; and
    the hierarchical volume area setting processing circuit controls the size of the next-step hierarchical volume area on the basis of the detected heteromorphic state.

3. The endoscope insertion support system according to claim 1, further including:
    a volume area altering processing circuit which extends or contracts a distance between end faces of the volume area.

4. The endoscope insertion support system according to claim 3, further including:
    a direction determining processing circuit which determines the extending/contracting direction of the volume area or the hierarchical volume area, wherein:
    the volume area altering processing circuit extends or contracts the distance between the end faces of the volume area or the hierarchical volume area on the basis of a result of determination by the direction determining section.

5. The endoscope insertion support system according to claim 1, wherein:
    the contained state determining processing circuit determines the contained state of the tubular path on the basis of detection of branching hole in the tubular path in an end face of the volume area or the hierarchical volume area.

6. The endoscope insertion support system according to claim 1, wherein:
    the contained state determining processing circuit determines the contained state of the tubular path on the basis of detection of the tubular organ on a side face of the volume area or the hierarchical volume area.

7. The endoscope insertion support system according to claim 1, further comprising:
    a route setting processing circuit which sets a line connecting gravity center points of tubular path sections at least in the vicinities of end faces of the volume area and the hierarchical volume area as an endoscope insertion support route.

8. The endoscope insertion support system according to claim 7, wherein:
the endoscopic insertion support route is set curvilinearly.

9. The endoscope insertion support system according to claim 1, further including:
a multiplanar reformation image generating processing circuit which generates a multiplanar reformation image in the subject on the basis of the three-dimensional image data of the subject; and
a start point designating processing circuit which designates the start point on the generated multiplanar reformation image.

10. The endoscope insertion support system according to claim 1, wherein:
coordinates of the start point designated by the start point coordinates designating processing circuit are coordinates contained in the volume area or the hierarchical volume area.

11. The endoscope insertion support system according to claim 1, wherein:
the tubular organ is one of bronchus, blood vessel, large intestine, small intestine, pancreas duct, bile duct or lymphatic vessel.

12. An endoscope insertion support method comprising the following steps executed by a computer:
a volume area setting step of setting a volume area which has a start point set in a tubular path of a tubular organ within three-dimensional image data of a subject stored in a storage device and has a size so prescribed as to contain the tubular organ;
an organ area information calculating step of extracting tubular area information in the volume area on the basis of the three-dimensional image data of the tubular organ in the volume area and calculating segmentation data representing a tubular path shape;
a contained state determining step of determining whether or not the tubular path is contained in the volume area set at the volume area setting step;
a heteromorphic state detecting step of detecting a strictured or expanded state of the tubular path, as a heteromorphic state, on the basis of at least one of a diameter, area and circumferential length out of the segmentation data calculated at the organ area information calculating processing step; and
a hierarchical volume area setting step of setting a hierarchical volume area obtained by being hierarchically arranged and linked to the volume area set at the volume area setting step to a size based on a result of determination at the contained state determining step.

* * * * *